US012665087B2

(12) United States Patent
    Godbole et al.

(10) Patent No.: US 12,665,087 B2
(45) Date of Patent: *Jun. 23, 2026

(54) SYSTEMS AND METHODS FOR MACHINE LEARNING FROM MEDICAL RECORDS

(71) Applicant: Insurance Services Office, Inc., Jersey City, NJ (US)

(72) Inventors: Sneha Godbole, Whittier, CA (US); Kate M. Riordan, Methuen, MA (US); Pei-Yau Lung, Winchester, MA (US); Shikha Bordia, Secaucus, NJ (US); Tushar Jain, New Delhi (IN); Gautam Kunapuli, Brooklyn, NY (US)

(73) Assignee: Insurance Services Office, Inc., Jersey City, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/417,695

(22) Filed: Jan. 19, 2024

(65) Prior Publication Data

US 2024/0221949 A1 Jul. 4, 2024

Related U.S. Application Data

(63) Continuation-in-part of application No. 17/732,322, filed on Apr. 28, 2022, now Pat. No. 12,562,283.

(Continued)

(51) Int. Cl.
*G16H 50/20* (2018.01)
*G16H 10/20* (2018.01)

(52) U.S. Cl.
CPC ............. *G16H 50/20* (2018.01); *G16H 10/20* (2018.01)

(58) Field of Classification Search
CPC ............................... G16H 50/20; G16H 10/20
See application file for complete search history.

(56) References Cited

U.S. PATENT DOCUMENTS

| | | |
|---|---|---|
| 7,587,182 B2 | 9/2009 | Kawai |
| 7,684,676 B2 | 3/2010 | Ando et al. |

(Continued)

FOREIGN PATENT DOCUMENTS

| | | |
|---|---|---|
| CN | 111326226 A | 6/2020 |
| WO | 2018/017467 A1 | 1/2018 |
| WO | 2020/124026 A1 | 6/2020 |

OTHER PUBLICATIONS

Munzert, Wiley 2015, excerpts, pp. xv-434.*

(Continued)

*Primary Examiner* — Michael I Ezewoko
(74) *Attorney, Agent, or Firm* — McCarter & English, LLP

(57) ABSTRACT

Systems and methods for machine learning of medical records are provided. The system can execute multiple machine learning models on the medical records in parallel using multi-threaded approach wherein each machine learning model executes using its own, dedicated computational thread in order to significantly speed up the time with which relevant information can be identified from documents by the system. The multi-threaded machine learning models can include, but are not limited to, sentence classification models, comorbidity models, ICD models, body parts models, prescription models, and provider name models. The system can also utilize combined convolutional neural networks and long short-term models (CNN+LSTMs) as well as ensemble machine learning models to categorize sentences in medical records. The system can also extract service provider, medical specializations, and dates of service information from medical records.

14 Claims, 35 Drawing Sheets

Related U.S. Application Data

(60) Provisional application No. 63/180,919, filed on Apr. 28, 2021.

(56) References Cited

U.S. PATENT DOCUMENTS

| | | | |
|---|---|---|---|
| 10,755,804 B2 * | 8/2020 | Katwala | G06F 40/169 |
| 10,770,180 B1 | 9/2020 | Kemp et al. | |
| 10,929,420 B2 | 2/2021 | Xu et al. | |
| 10,957,433 B2 | 3/2021 | Lucas et al. | |
| 11,042,712 B2 | 6/2021 | Prakash et al. | |
| 11,062,704 B1 | 7/2021 | Kodish-Wachs | |
| 11,151,982 B2 | 10/2021 | Tomkins et al. | |
| 11,487,902 B2 | 11/2022 | Ardhanari et al. | |
| 11,488,713 B2 | 11/2022 | Velez et al. | |
| 11,538,112 B1 | 12/2022 | Singh et al. | |
| 11,545,242 B2 | 1/2023 | Aravamudan et al. | |
| 11,557,276 B2 | 1/2023 | Bender et al. | |
| 11,580,455 B2 | 2/2023 | Sarferaz | |
| 11,646,032 B2 | 5/2023 | Balasubramaniam et al. | |
| 11,670,408 B2 | 6/2023 | Pinto | |
| 11,670,420 B2 | 6/2023 | Ling et al. | |
| 11,676,735 B2 | 6/2023 | Wang et al. | |
| 11,705,226 B2 * | 7/2023 | Colley | G16H 50/20 705/3 |
| 11,727,284 B2 | 8/2023 | Le Biannic | |
| 11,777,815 B1 | 10/2023 | Ambale Srinivasamurthy et al. | |
| 11,810,331 B2 | 11/2023 | Jiang et al. | |
| 11,915,822 B2 | 2/2024 | Yi et al. | |
| 2018/0018966 A1 | 1/2018 | Leonard | |
| 2018/0046764 A1 * | 2/2018 | Katwala | G16H 15/00 |
| 2018/0068074 A1 | 3/2018 | Shen | |
| 2019/0065464 A1 | 2/2019 | Finley et al. | |
| 2019/0347269 A1 | 11/2019 | Xu et al. | |
| 2020/0185102 A1 | 6/2020 | Leventhal et al. | |
| 2020/0222010 A1 | 7/2020 | Howard | |
| 2020/0334416 A1 | 10/2020 | Vianu et al. | |
| 2020/0365243 A1 | 11/2020 | Swisher et al. | |
| 2020/0402625 A1 | 12/2020 | Aravamudan et al. | |
| 2021/0057068 A1 | 2/2021 | Dandala et al. | |
| 2021/0125721 A1 | 4/2021 | Kemp et al. | |
| 2021/0272571 A1 | 9/2021 | Balasubramaniam et al. | |
| 2021/0327582 A1 | 10/2021 | Joshi | |
| 2021/0343411 A1 | 11/2021 | Zhang et al. | |
| 2022/0075944 A1 | 3/2022 | Du et al. | |
| 2022/0115134 A1 | 4/2022 | Strader et al. | |
| 2022/0319219 A1 | 10/2022 | Tsibulevskiy et al. | |
| 2022/0351868 A1 | 11/2022 | Godbole et al. | |
| 2022/0375605 A1 | 11/2022 | Lipton et al. | |
| 2022/0398374 A1 | 12/2022 | Chowdhury et al. | |
| 2023/0084146 A1 | 3/2023 | Singh et al. | |
| 2025/0131184 A1 | 4/2025 | Chen et al. | |

OTHER PUBLICATIONS

Office Action dated Mar. 19, 2025, issued in connection with U.S. Appl. No. 17/732,322 (24 pages).

International Search Report of the International Searching Authority mailed on Apr. 9, 2025, issued in connection with International Application No. PCT/US25/011963 (5 pages).

Written of the International Searching Authority mailed on Apr. 9, 2025, issued in connection with International Application No. PCT/US25/011963 (7 pages).

International Search Report of the International Searching Authority mailed on Sep. 8, 2022, issued in connection with International Application No. PCT/US22/26817 (3 pages).

Written Opinion of the International Searching Authority mailed on Sep. 8, 2022, issued in connection with International Application No. PCT/US22/26817 (8 pages).

Singh, et al., "An Ensemble Approach for Extractive Text Summarization," International Conference on Emerging Trends in Information Technology and Engineering, Apr. 2020, https://www.researchgate.net/profile/prateek-chikara/publication/340967651_An_Esemble_Approach_for_Extractive_Text_Summarization/links/5fa1087592851c14bcff503e/An-Ensemble-Approach-for-Extractive-Text-Summarization.pdf (8 pages).

Trivedi, et al., "Repurposing Entailment for Multi-Hop Question Answering Tasks," arXiv:1904.09380, Apr. 2019, https://arxiv.org/pdf/1904.09380 (11 pages).

Office Action dated May 14, 2024, issued in connection with U.S. Appl. No. 17/732,322 (20 pages).

Extended European Search Report dated Feb. 20, 2025, issued by the European Patent Office in connection with European Patent Application No. 22796766.8 (12 pages).

Polap, et al., "Agent Architecture of an Intellgient Medical System Based onn Federated Learning and Blockchain Technology," Journal of Information Security and Applications (2021) (8 pages).

Notice of Allowance dated Sep. 16, 2025, issued in connection with U.S. Appl. No. 17/732,322 (14 pages).

International Search Report of the International Searching Authority mailed on Nov. 4, 2025, issued in connection with International Application No. PCT/US25/042371 (5 pages).

Written Opinion of the International Searching Authority mailed on Nov. 4, 2025, issued in connection with International Application No. PCT/US25/042371 (8 pages).

* cited by examiner (A) → start_model_thread is Created ——266——　270——→ Model monitor (B) →

276 ——

274 ——

(C) → Is sentence classification model? —Yes→ Create and start thread with timeout to process document through sentence classification models → 278 —— Execute sentence classification workflow → (E)

No ↓

290 ——

Is comorbidity model? —Yes→ 292 —— Create and start thread with timeout to process document through comorbidity tagging model → 294 —— Execute comorbidity tagging workflow → (F)

No ↓

298 ——

Is ICD model? —Yes→ 300 —— Create and start thread with timeout to process document through ICD tagging model → 302 —— Execute ICD tagging workflow → (G)

No ↓

306 ——

Is body parts model? —Yes→ 308 —— Create and start thread with timeout to process document through body parts tagging model → 310 —— Execute body parts tagging workflow → (H)

No ↓

314 ——

Is Rx model? —Yes→ 316 —— Create and start thread with timeout to process document through Rx tagging model → 318 —— Execute Rx tagging workflow → (I)

No ↓

322 ——

(D) ← No — Is Provider name model? —Yes→ 324 —— Create and start thread with timeout to process document through Provider name model → 326 —— Execute Provider name tagging workflow → (J)

FIG. 5 (Cont.)

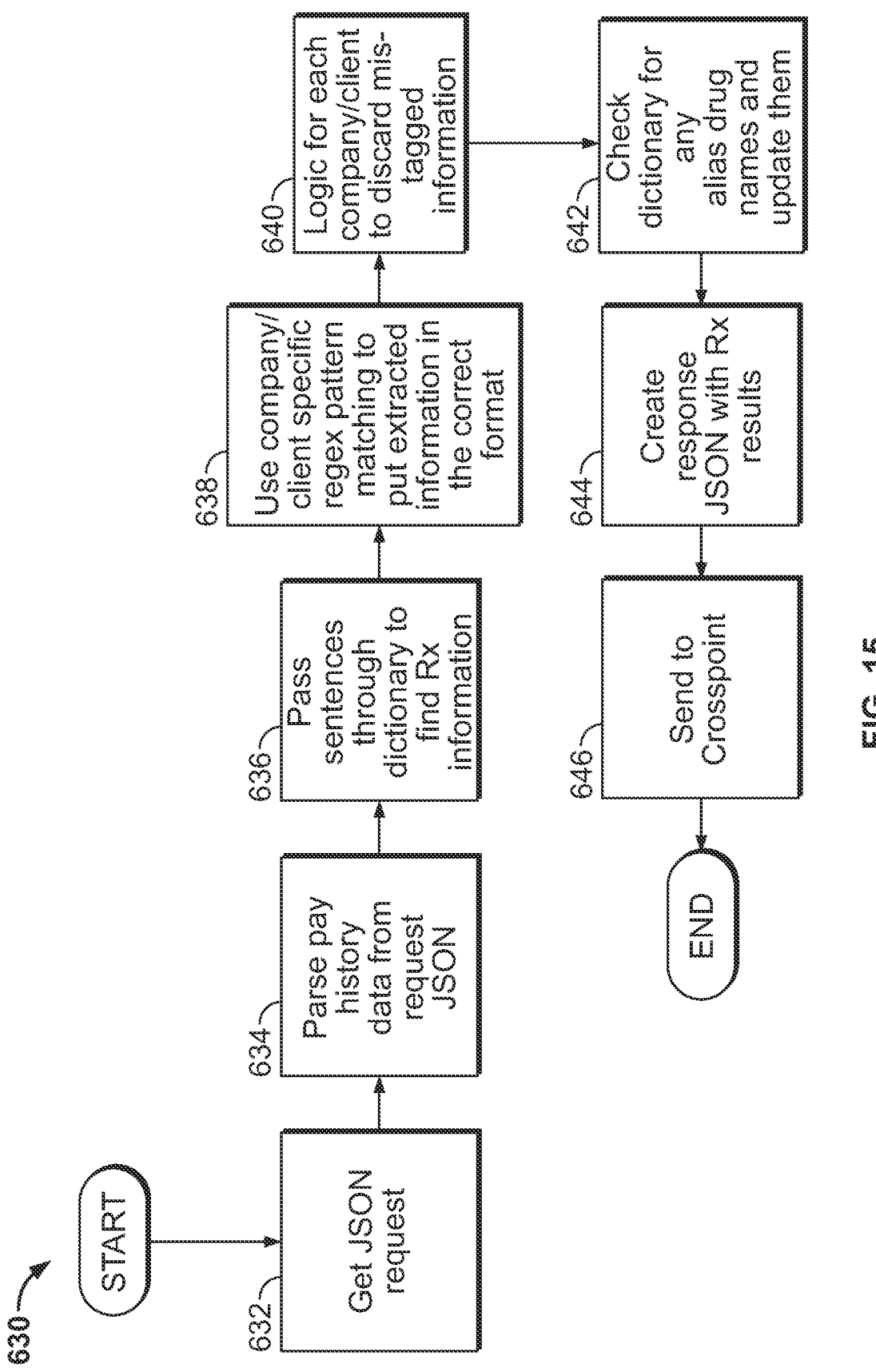

START

632 — Get JSON request

634 — Parse pay history data from request JSON

636 — Pass sentences through dictionary to find Rx information

638 — Use company/client specific regex pattern matching to put extracted information in the correct format 640 — Logic for each company/client to discard mis-tagged information 642 — Check dictionary for any alias drug names and update them 644 — Create response JSON with Rx results 646 — Send to Crosspoint

END

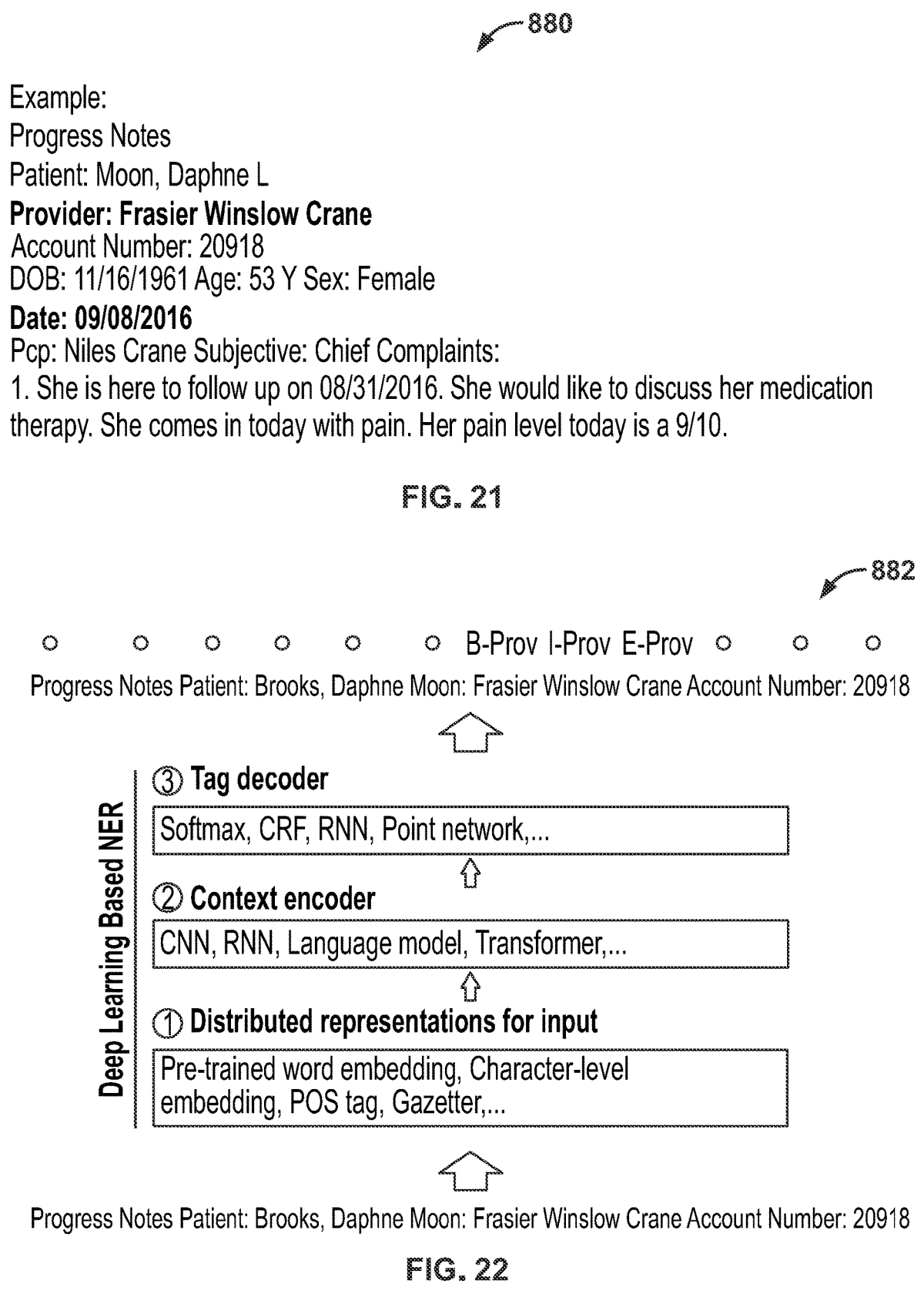

880

Example:
Progress Notes
Patient: Moon, Daphne L
Provider: Frasier Winslow Crane
Account Number: 20918
DOB: 11/16/1961 Age: 53 Y Sex: Female
Date: 09/08/2016
Pcp: Niles Crane Subjective: Chief Complaints:
1. She is here to follow up on 08/31/2016. She would like to discuss her medication therapy. She comes in today with pain. Her pain level today is a 9/10.

○     ○     ○     ○     ○     ○  B-Prov I-Prov E-Prov  ○     ○     ○

Progress Notes Patient: Brooks, Daphne Moon: Frasier Winslow Crane Account Number: 20918

⇧

Deep Learning Based NER

③ Tag decoder

| Softmax, CRF, RNN, Point network,... |
| --- |

⇧

② Context encoder

| CNN, RNN, Language model, Transformer,... |
| --- |

⇧

① Distributed representations for input

| Pre-trained word embedding, Character-level embedding, POS tag, Gazetter,... |
| --- |

⇧

Progress Notes Patient: Brooks, Daphne Moon: Frasier Winslow Crane Account Number: 20918

FIG. 22

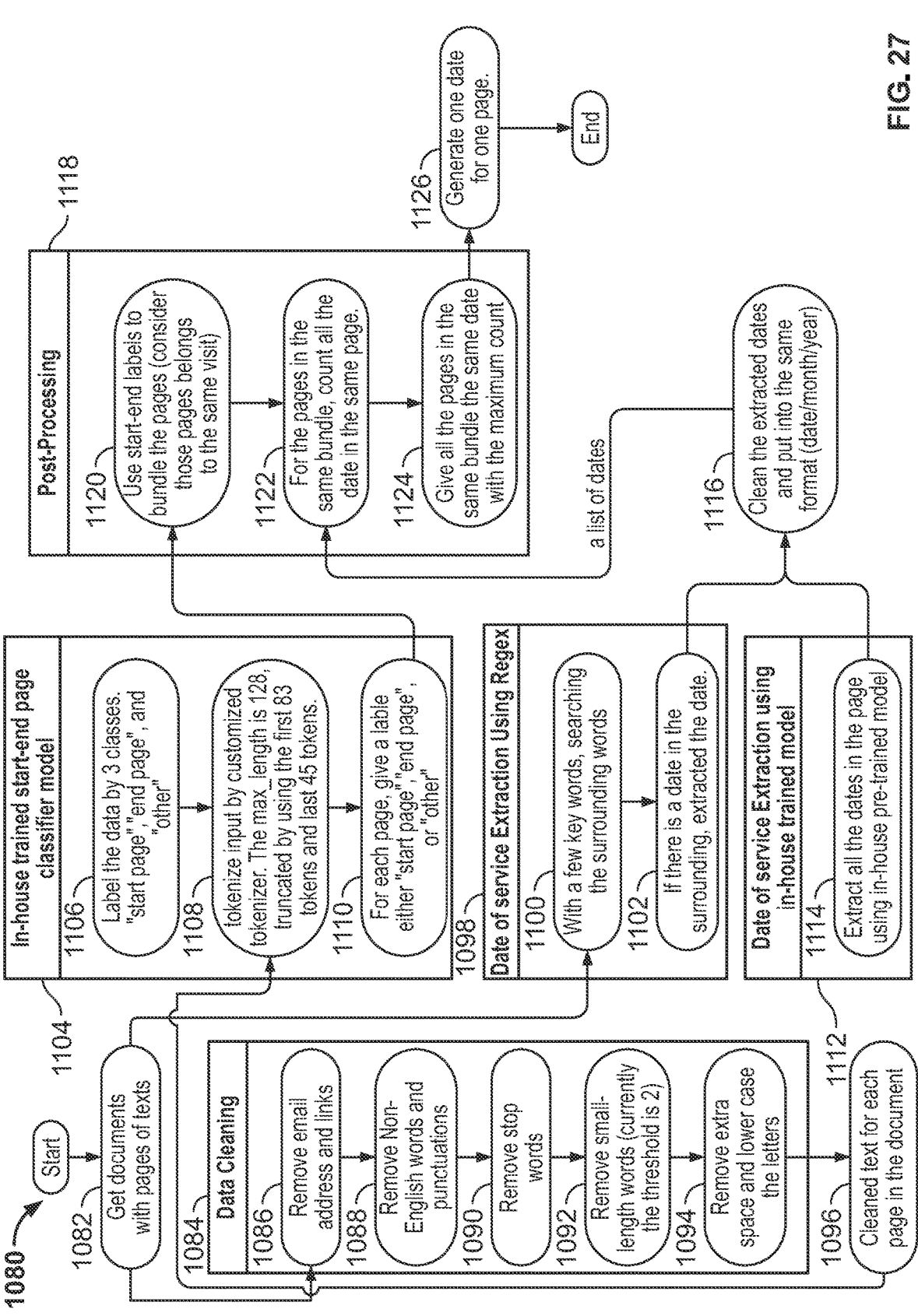

Start — 1082

Get documents with pages of texts — 1084

Data Cleaning

Remove email address and links — 1086

Remove Non-English words and punctuations — 1088

Remove stop words — 1090

Remove small-length words (currently the threshold is 2) — 1092

Remove extra space and lower case the letters — 1094

Cleaned text for each page in the document — 1096

In-house trained start-end page classifier model — 1104

Label the data by 3 classes. "start page", "end page", and "other" — 1106 tokenize input by customized tokenizer. The max_length is 128, truncated by using the first 83 tokens and last 45 tokens. — 1108

For each page, give a lable either "start page", "end page", or "other" — 1110

Date of service Extraction Using Regex — 1098

With a few key words, searching the surrounding words — 1100

If there is a date in the surrounding, extracted the date. — 1102

Date of service Extraction using in-house trained model — 1112

Extract all the dates in the page using in-house pre-trained model — 1114 a list of dates

Clean the extracted dates and put into the same format (date/month/year) — 1116

Post-Processing — 1118

Use start-end labels to bundle the pages (consider those pages belongs to the same visit) — 1120

For the pages in the same bundle, count all the date in the same page. — 1122

Give all the pages in the same bundle the same date with the maximum count — 1124

Generate one date for one page. — 1126

End

SYSTEMS AND METHODS FOR MACHINE LEARNING FROM MEDICAL RECORDS

RELATED APPLICATIONS

This application is a continuation-in-part of, and claims priority to, U.S. patent application Ser. No. 17/732,322 filed Apr. 28, 2022, which claims the benefit of priority to U.S. Provisional Application Ser. No. 63/180,919 filed on Apr. 28, 2021, the entire disclosures of which are expressly incorporated herein by reference.

FIELD OF THE INVENTION

The present invention relates generally to the field of machine learning. More specifically, the present invention relates to systems and methods for machine learning from medical records.

RELATED ART

In the medical and insurance claims processing fields, accurate processing of medical claims is paramount. Such accurate processing is critical to ensuring that only valid claims are processed, thereby minimizing losses for insurance carriers and ensuring that medical personnel are adequately compensated for their procedures.

The field of machine learning has increasingly grown in sophistication and applicability to heavily data-intensive analytical tasks. While machine learning has, in the past, been applied to analyze medical claims records, such efforts have largely failed because the machine learning systems cannot adequately identify wide varieties of patterns in medical data, such as identifying comorbidity terms, ICD codes, body part information, prescription information, and other useful types of information. Additionally, existing machine learning systems cannot reliably parse medical records stored in various forms, such as nursing records and other types of records. Still further, existing machine learning systems cannot easily and rapidly process medical records, often requiring significant computational time and complexity in order to identify only sparse types of information from medical records. In short, they cannot identify a rich multiplicity of different types of information from medical records with reduced computational time and intensity.

Accordingly, what would be desirable are systems and methods for machine learning of medical records which address the foregoing, and other, shortcomings in existing machine learning systems.

SUMMARY

The present disclosure relates to systems and methods for machine learning of medical records. The system processes a wide array of medical records, including, but not limited to, nursing records and other records, in order to identify relevant information from such records. The system can execute multiple machine learning models on the medical records in parallel using multi-threaded approach wherein each machine learning model executes using its own, dedicated computational thread in order to significantly speed up the time with which relevant information can be identified from documents by the system. The multi-threaded machine learning models can include, but are not limited to, sentence classification models, comorbidity models, ICD models, body parts models, prescription models, and provider name models, all of which can execute in parallel using dedicated computational processing threads executed by one or more processing systems (e.g., one or more back-end processing servers). The system can also utilize combined convolutional neural networks and long short-term models (CNN+LSTMs) as well as ensemble machine learning models to categorize sentences in medical records. The system can also extract service provider, medical specializations, and dates of service information from medical records.

BRIEF DESCRIPTION OF THE DRAWINGS

The foregoing features of the invention will be apparent from the following Detailed Description, taken in connection with the accompanying drawings, in which:

FIG. 15 is a flowchart illustrating machine learning processes carried out by the system of the present disclosure for determining a prescription payment history from medical records;

FIG. 21 is a diagram illustrating a medical record to which joint sequence labelling is applied by the systems and methods of the present disclosure;

FIG. 22 is a diagram illustrating processing steps carried out by the systems and methods of the present disclosure for joint sequence labelling of the medical record illustrated in FIG. 21;

FIG. 27 is a flowchart illustrating additional processing steps carried out by the systems and methods of the present disclosure for date extraction and sorting of medical records.

DETAILED DESCRIPTION

The present disclosure relates to machine learning systems and methods for machine learning from medical records, as discussed in detail below in connection with FIGS. 1-27.

Figure 1:
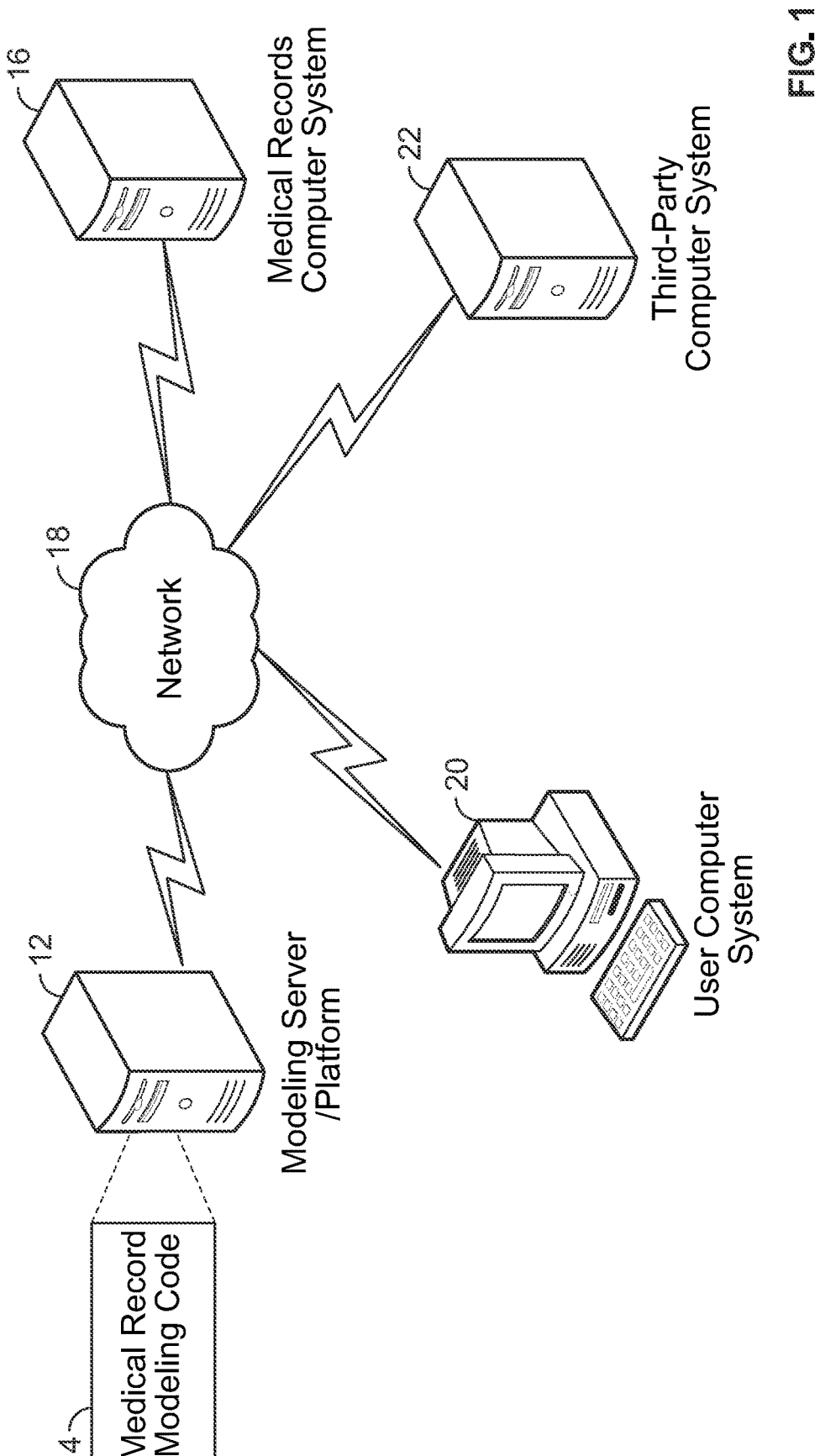
FIG. 1 is a diagram illustrating the system of the present disclosure.

FIG. 1 is a diagram illustrating the system of the present disclosure, indicated generally at 10. The system 10 includes a modeling server/platform computer system 12 that executes medical record modeling software code 14 in order to perform the machine learning processes discussed herein from medical records such as nurse summaries, doctor summaries, medical claims data, insurance claims data, or other suitable data sources. The system 12 can communicate with a medical records computer system 16 via a network connection 18 in order to obtain the medical records therefrom. The medical records computer system 16 could include, but is not limited to, any of a computer system of a medical insurer, a medical provider, a government agency, or other party that is responsible for storing and managing medical records and/or insurance records relating thereto. Additionally, the system 12 can communicate with an end-user computer system 20 where a user of the system can access the machine learning features (and learned outputs) described herein, as well as a third-party computer system 22 which could be operated by one or more third parties interested in utilizing the machine learning features provided by the system 12.

The computer systems 12, 16, and 22 could comprise one or more computer servers and/or cloud-based platforms capable of supporting the various software and/or database functions described herein. Additionally, the end-user computer system 20 could include, but is not limited to, a personal computer, a laptop computer, a tablet computer, a smart telephone, or any other suitable computing device capable of accessing the machine learning features (and outputs) provided by the system 12. The network 18 could include, but is not limited to, a wired network (e.g., the Internet, a local area network (LAN), a wide area network (WAN), etc.) or wireless communications network (e.g., a WiFi network, a cellular network, an optical communications network, etc.). The modeling code 14 comprises specially-programmed, non-transitory, computer-readable instructions carried out by the system 12 for machine learning of various type of information from medical records (e.g., from medical records stored in the system 12 and transmitted to the system 12 for processing, medical records provided by the third-party computer system 22 and transmitted to the system 12 for processing, and/or medical records stored directly on the system 12 and processed thereby). The modeling code 14 could be programmed in any suitable high- or low-level programming language, including, but not limited to, Java, C, C++, C#, Python, Ruby, or any other suitable programming language, and the code could be stored in a non-transitory memory of the system 12 (e.g., in random-access memory (RAM), read-only memory (ROM), EEPROM, flash memory, disk, tape, field-programmable gate array (FPGA), application-specific integrated circuit (ASIC), etc.) and executed by one or more processors (e.g., microprocessors, central processing units (CPUs), microcontrollers, etc.) of the system 12. The specific functions performed by the code 12 are discussed in greater detail below in connection with FIGS. 2-16.

Figure 2A:
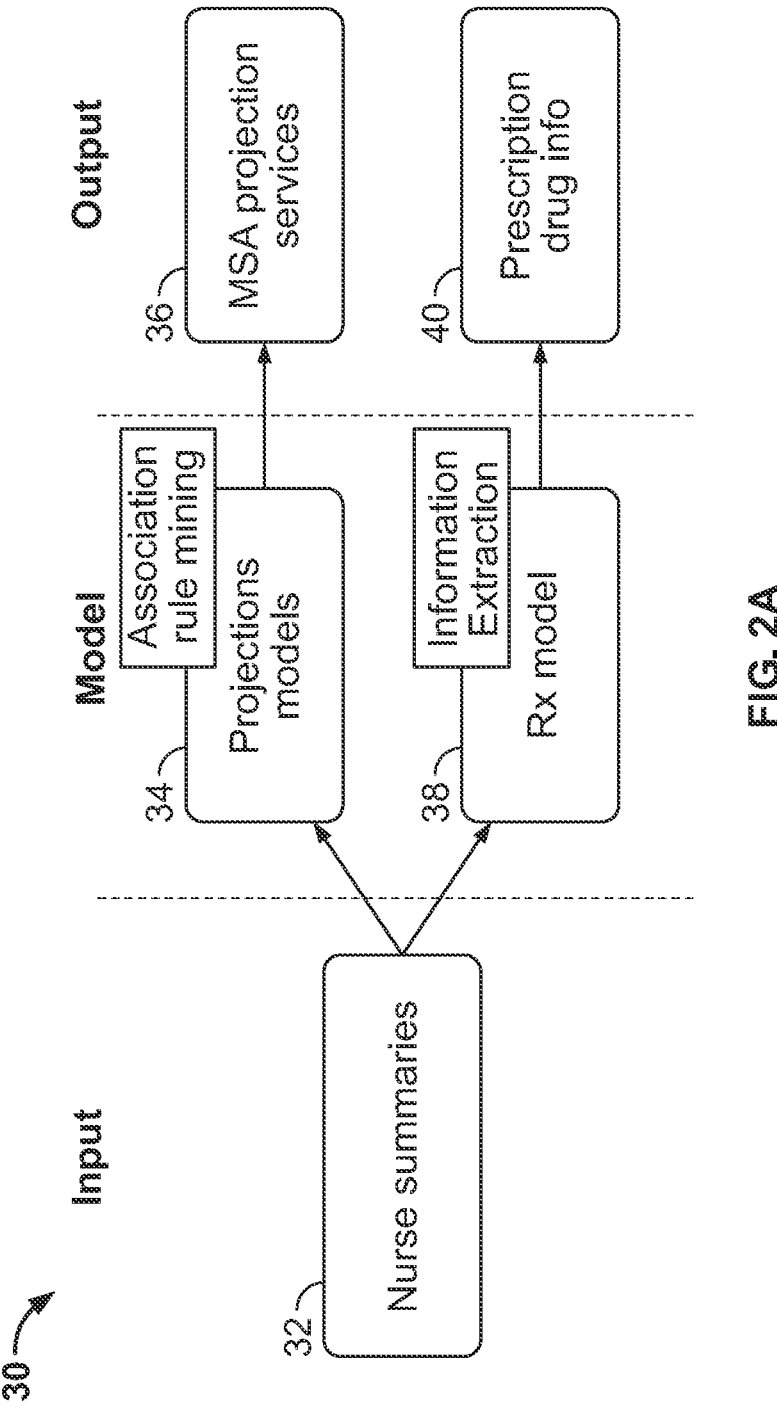
FIGS. 2A-2B are diagrams illustrating modelling processes carried out by the system of the present disclosure.
Figure 2B:
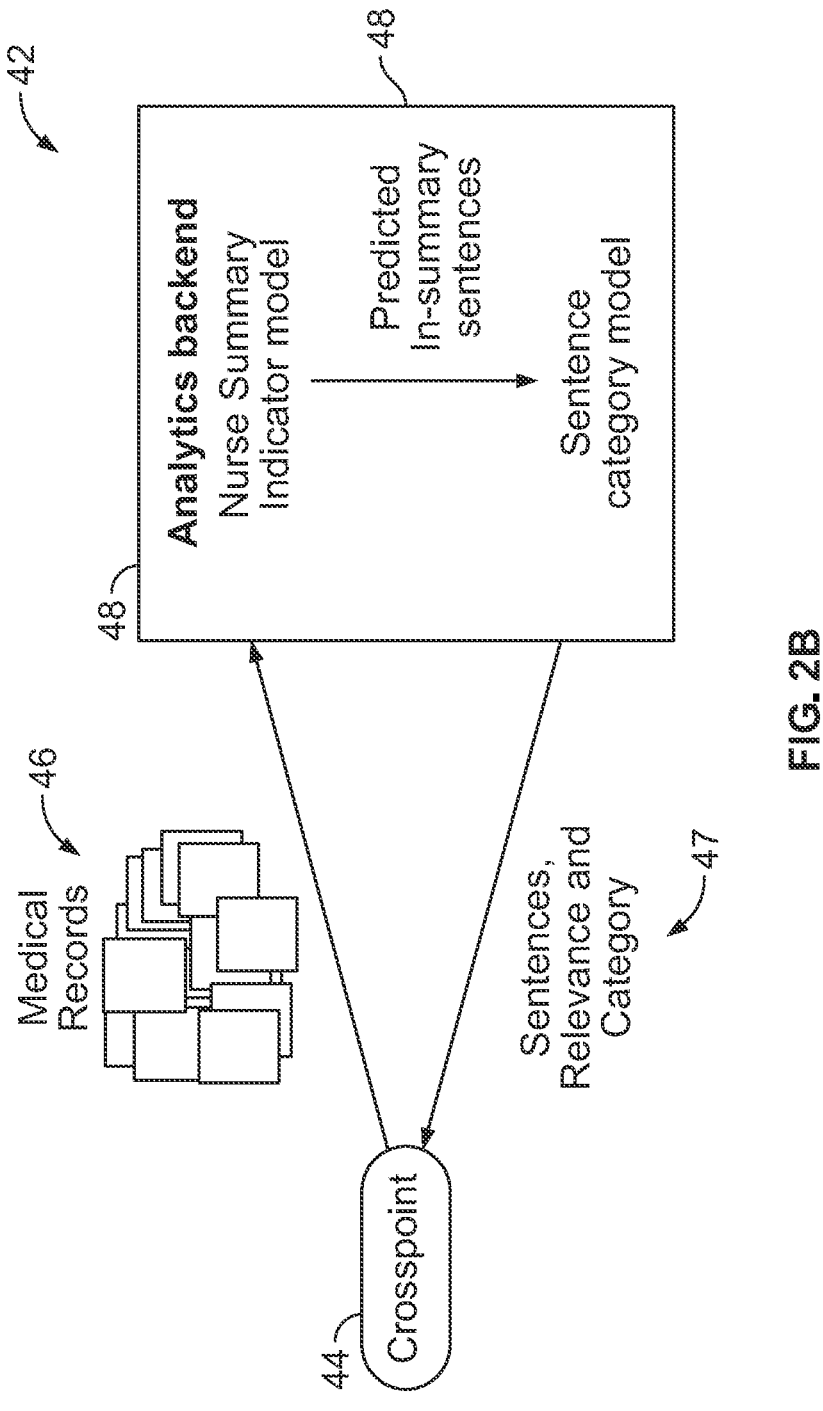

FIGS. 2A-2B are diagrams illustrating machine learning/modeling processes 30, 42 carried out by the system of the present disclosure. As shown in FIG. 2A, process 30 involves inputting into the system of one or more medical records such as nurse summaries 32, modeling of the medical records using a projections model 34 that implements association rule mining techniques and a prescription ("Rx") model 38 that performs information extraction from the medical records, and generating machine learning outputs from the modeling such as Medicare set-aside ("MSA") projections 36 and prescription drug information 40. Of course, the system can process other types of medical records beyond the nurse summaries 32, and can generate other types of output based upon machine learning techniques performed on the medical records.

As illustrated in FIG. 2B, the machine learning/modeling process 42 can include learning from medical records 46 provided by a data source 44 (such as a data exchange platform noted in FIG. 2B (referred to periodically in the drawings as the "CrossPoint" system, or other suitable data exchange platform)) using an analytics back-end 48 (which could execute on the computer system 12 of FIG. 1) to extract useful outputs 47 from the medical records 46 such as sentences, relevance of terms, and categories of terms. The back-end 48 could execute a number of customized machine learning models discussed herein, including, but not limited to, a nurse summary indicator model that predicts in-summary sentences from nurse records, as well as a sentence category model. Of course, the back-end 48 could execute other machine learning models if desired. Additionally, it is noted that the medical records 46 could be obtained using optical character recognition (OCR) applied to scanned documents.

Figure 3A:
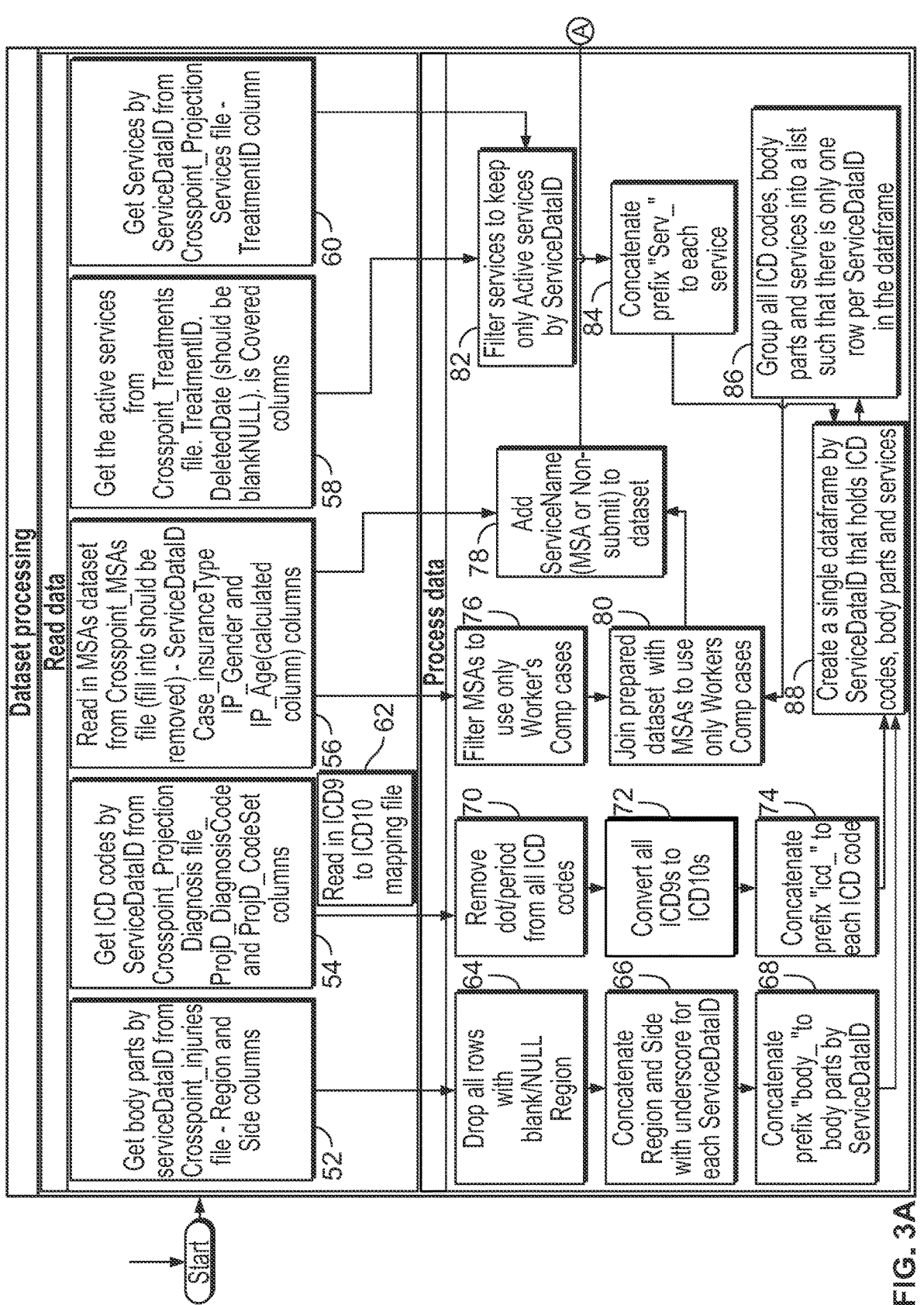
FIGS. 3A-3B are flowcharts illustrating processing steps carried out by the system of the present disclosure for projections modeling from medical records.
Figure 3A:
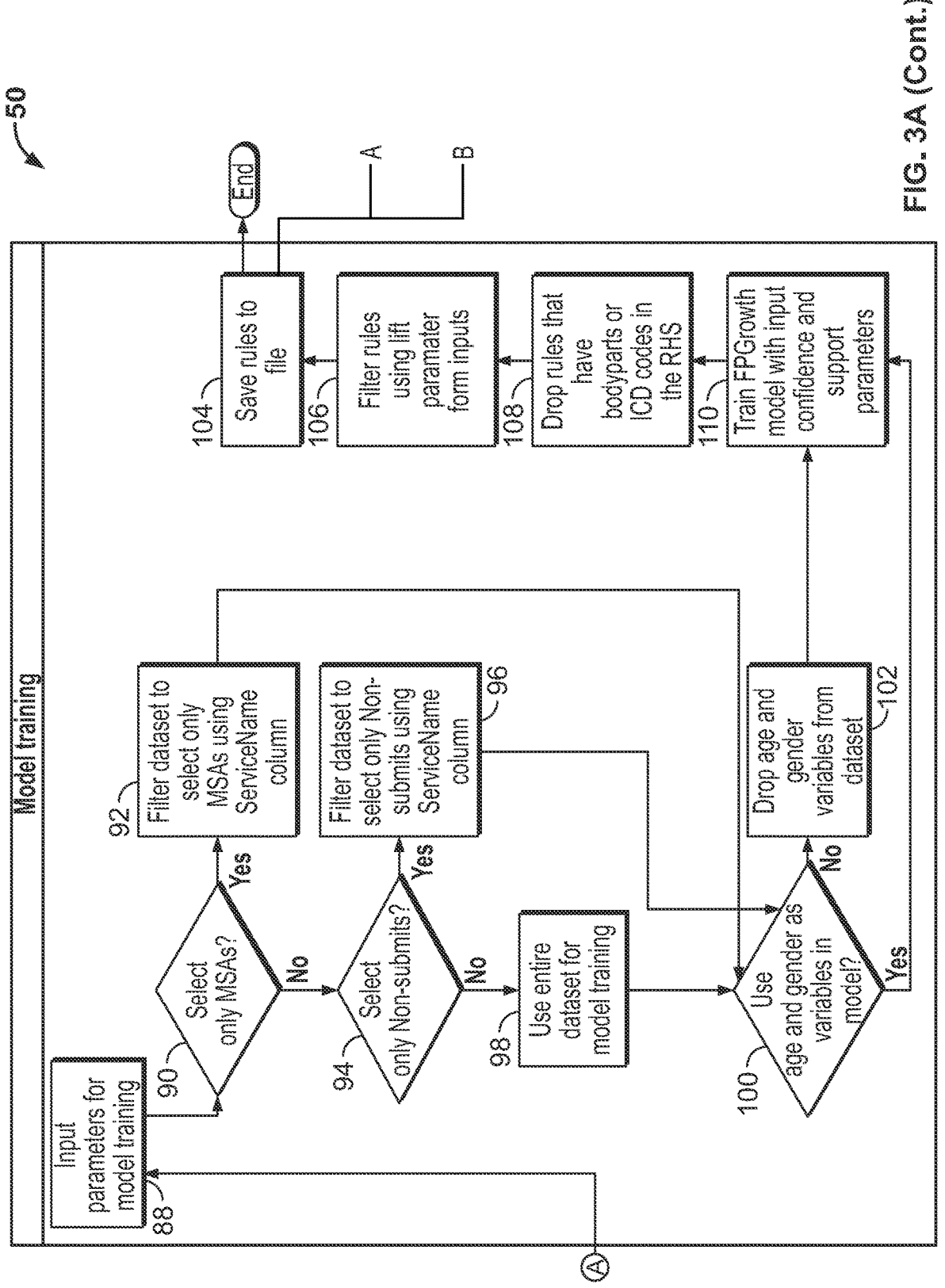
Figure 3B:
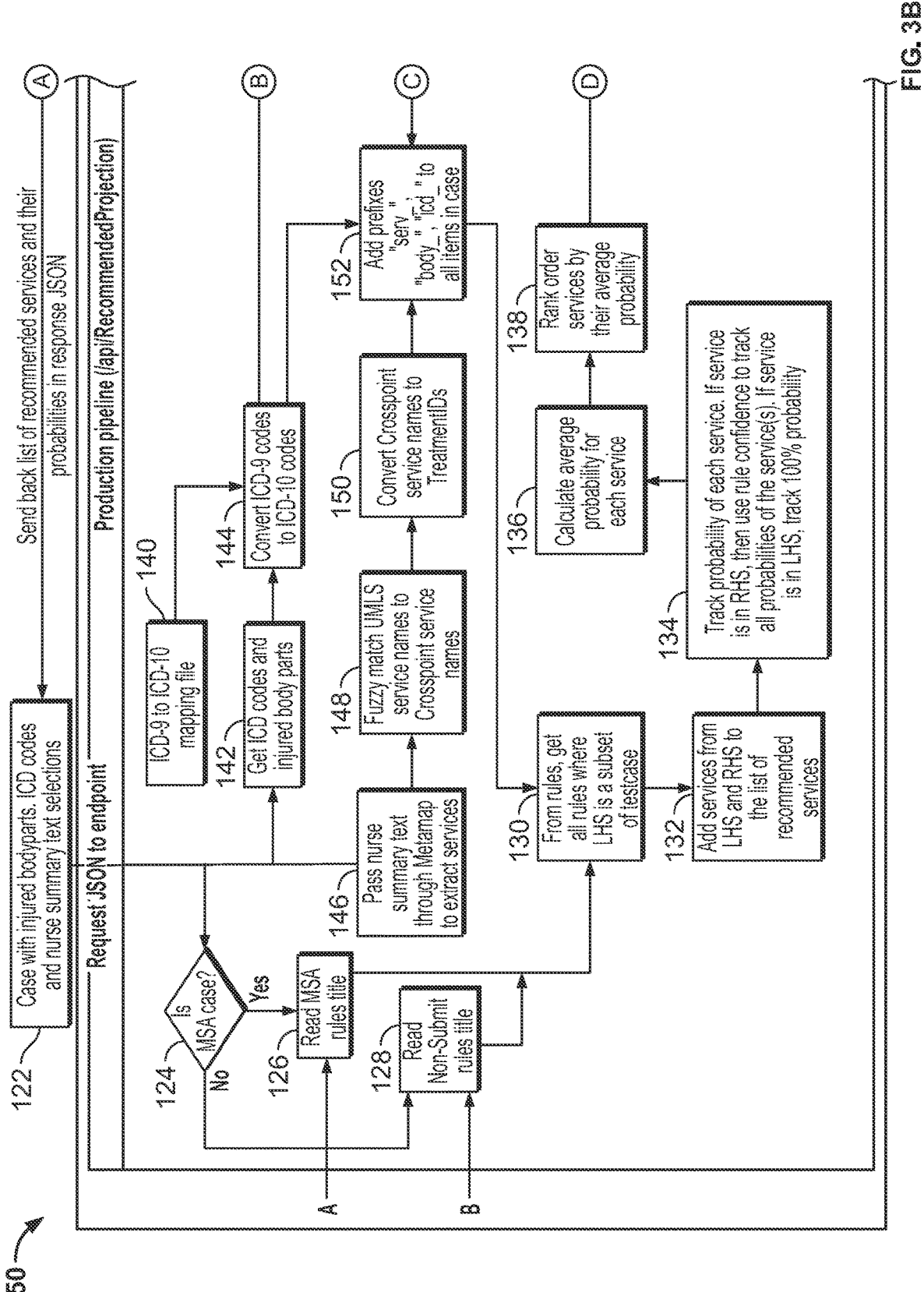
Figure 3B:
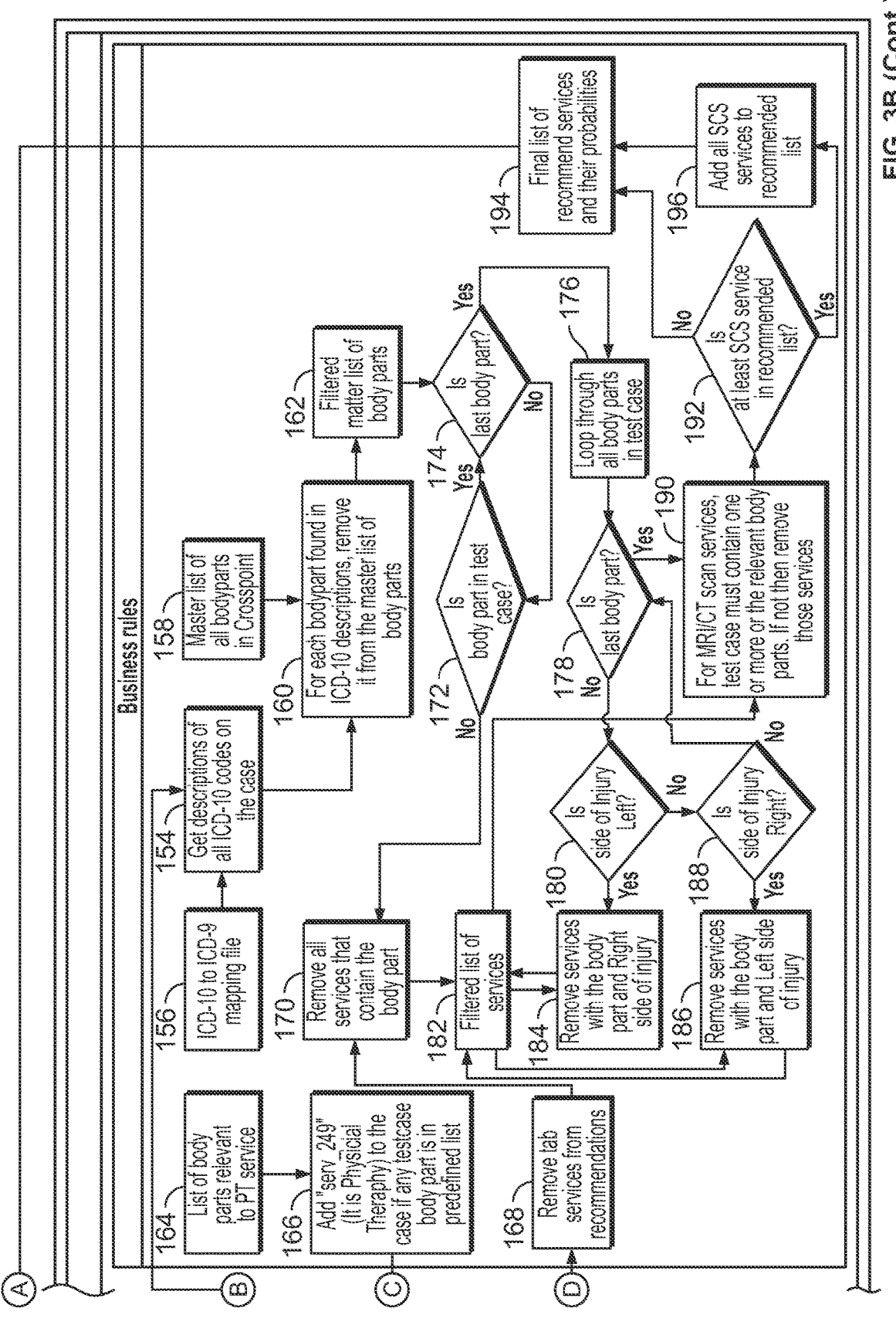

FIGS. 3A-3B are flowcharts illustrating processing steps, indicated generally at 50, carried out by the system of the present disclosure for projections modeling from medical records. Specifically, the steps 50 are carried out by the projections models 34 of FIG. 2A, and allow the system to generate MSA projections 36 of FIG. 2A. Beginning in step 52, the system begins reading medical record data by reading body parts data from the medical records data. Additionally, in step 54, the system reads ICD codes from the medical records data, and in step 56, the system reads MSA dataset data from the medical records. Still further, in step 58, the system reads active services from the medical records, and in step 60, the system reads services from the medical records. Also, in step 62, the system reads International Statistical Classification of Diseases and Related Health Problems ("ICD") data corresponding to ICD9 format and maps the data to ICD10 format (into an ICD10 mapping file). Steps 52-62 can be carried out concurrently, if desired, and represent data reading operations performed by the system on the medical records data.

In steps 64-86, the system processes the data read in steps 52-62. Specifically, in step 64, the system processes the body parts data read in step 52 so that all blank or null rows of data are removed from the body parts data. Then, in step 66, the system concatenates region and state data (and optionally, underlines such data) from the body parts data. Then, in step 68, a prefix is appended to the concatenated data, such as a "body_" prefix. In step 70, the system processes the ICD data to remove punctuation (e.g., dots or periods) from all ICD codes. Then, in step 72, the system converts all ICD9-formatted codes into ICD10-formatted codes. In step 74, the system appends a prefix to the concatenated data, such as a "icd_" prefix.

In step 76, the system filters all MSAs from the MSA dataset read in step 56 so that only workers' compensation cases are included in the dataset. In step 82, the system filters the services data read in steps 58 and 60 to that only active services are retained. Then, in step 84, the system appends a prefix, such as a "serv_" prefix, to the active services data.

In step 88, the system creates a single data frame using the data generated in steps 68, 74, and 84 which stores ICD codes, body parts, and services data. Then, in step 86, the system groups the ICD codes, body parts, and services data into a list such that there is only one row per identifier of a service in the database. In step 80, the system processes the outputs of steps 76 and 86 to join the prepared dataset with the MSAs to use only workers' compensation cases. In step 78, the system adds a service name to the data set.

In steps 88-110, the system performs training of the machine learning model. In step 88, the system inputs parameters for model training, using the data generated in step 78. Then, in step 90, a determination is made as to whether to select only data relating to MSAs. If so, step 92 occurs, wherein the system filters the dataset to select only MSAs using a service name identifier (stored in a column). Then, step 100 occurs, wherein a determination is made as to whether to use age or gender as variables in the model. If a negative determination is made, step 102 occurs, wherein the system drops age and gender variables from the data set. Then, in step 110, the system trains a machine learning model with input confidence and support parameters. If a positive determination is made in step 100, processing proceeds directly to step 110. In step 108, after training is complete, the system drops rules that have body parts or ICD codes in the right-hand side ("RHS"). Then, in step 106, the system filters rules using lift parameters from the inputs. Lift parameters indicate the importance of a rule, such that a value below 1.0 indicates that the rule is not significant to give a good prediction, while values above 1.0 indicate increasing importance of the rule and ability to provide good predictions. A threshold value can be set or the lift values and the generated rules can be filtered to allow for better predictions. Then, step 104 occurs, wherein the system saves the rules to a file.

If a negative determination is made in step 90, step 94 occurs, wherein a determination is made as to whether to select only worker's compensation claims that are not required to be submitted for review in accordance with specific approval rules (referred to as "non-submits"). If so, step 96 occurs, wherein the system filters the data set to select only non-submits using the name of the service, and control proceeds to step 100. Otherwise, if a negative determination is made in step 94, step 98 occurs, wherein the system uses the entire data set for model training. Then, control proceeds to step 100.

In step 122 (see FIG. 3B), the system retrieves cases that include injured body parts, ICD codes, and nurse summary text sections. In step 124, a decision is made as to whether the current case is an MSA case. If a positive decision is made, step 126 occurs, wherein the system reads the MSA rules file. Otherwise, step 128 occurs, wherein the system reads the non-submit rules files. In step 130, the system retrieves from the rules all rules where the left-hand side ("LHS") is a subset of a test case. Specifically, the format of association rules is a list of rules (equivalent to rows in a spreadsheet) with two sides (left and right sides, equivalent to columns in a spreadsheet). Then, in step 132, the system adds services from LHS and right-hand side ("RHS") to the list of recommended services. In step 134, the system tracks the probability of each service. If the service is in RHS, the system uses the rule confidence to track all probabilities of the services. If the service is in LHS, the system tracks the probability at 100%. In step 136, the system calculates the average probability for each service. In step 138, the system ranks the order of services by their average probabilities. Control then passes to step 168, discussed below.

In step 140, the system performs an ICD9 to IDC10 mapping. In step 142, the system obtains ICD codes and injured body parts. In step 144, the system converts ICD-9 codes to ICD-10 codes. In step 146, the system passes nurse summary text information through a metamap to extract service information. Then, in step 148, the system performs a fuzzy match of Unified Medical Language System ("UMLS") service names to service names stored in a platform (e.g., a data exchange platform). Then, in step 150, the system converts the platform service names to treatment identifiers. In step 152, the system adds prefixes (such as "serv_" and "body_" and "icd_" to all items in the case, and control passes to step 130.

In steps 154-196, the system applies a plurality of business rules to the case data. In step 154, the system obtains descriptions of all ICD-10 codes in the case. In step 156, the system performs an IDC-10 to ICD-9 mapping (e.g., using a mapping file). In step 158, the system creates a master list of all body parts. In step 160, the system removes each body part from the master list of all body parts where the body part matches an ICD-10 description. In step 162, the system generates a filtered master list of body parts. In step 164, the system generates a list of body parts that are relevant to physical therapy (PT) service. In step 166, the system adds a designator to the case (e.g., "serv_249") if any test case body part is in a predefined list. In step 168, the system removes lab services from the recommendations. Examples of lab services include, but are not limited to, urine drug screen, complete blood count (CBC) labs, comprehensive metabolic lab panels, and/or venipuncture labs. In step 174, the system makes a determination as to whether the last body party in the case has been processed. If a negative determination is made, step 172 occurs, wherein a determination is made as to whether the body part is in the text case. If a negative determination is made, step 170 occurs, wherein the system removes all services that contain the body part.

If a negative determination is made in step 174, step 176 occurs, wherein the system loops through all body parts in the test case. In step 178, a determination is made as to whether the last body part has been identified. If a negative determination is made, step 180 occurs, wherein a determination is made as to whether the injury is on the left side of the body, If so, steps 184 and 182 occur wherein the system filters the list of services and removes services with the body part and injuries occurring on the right side of the body. In the event of a negative determination in step 180, step 188 occurs, wherein a determination is made as to whether the injury is on the right side of the body. If so, steps 182 and 186 occur, wherein the system filters the list of services and removes services involving the body part and occurring on the left side of the body.

If a positive determination is made in step 178, step 190 occurs wherein a rule is enforced whereby the test case must contain one or more of the relevant body parts for MRI/CT scan services, and if not, such services are removed. In step 192, a decision is made as to whether at least one spinal cord stimulator ("SCS") service is in the recommended list. If a negative determination is made, step 194 occurs, wherein the final list of recommended services and their probabilities are generated and control returns to step 122. Otherwise, step 196 occurs, wherein all SCS services are added to the recommended list, and control passes to step 194.

Figure 4:
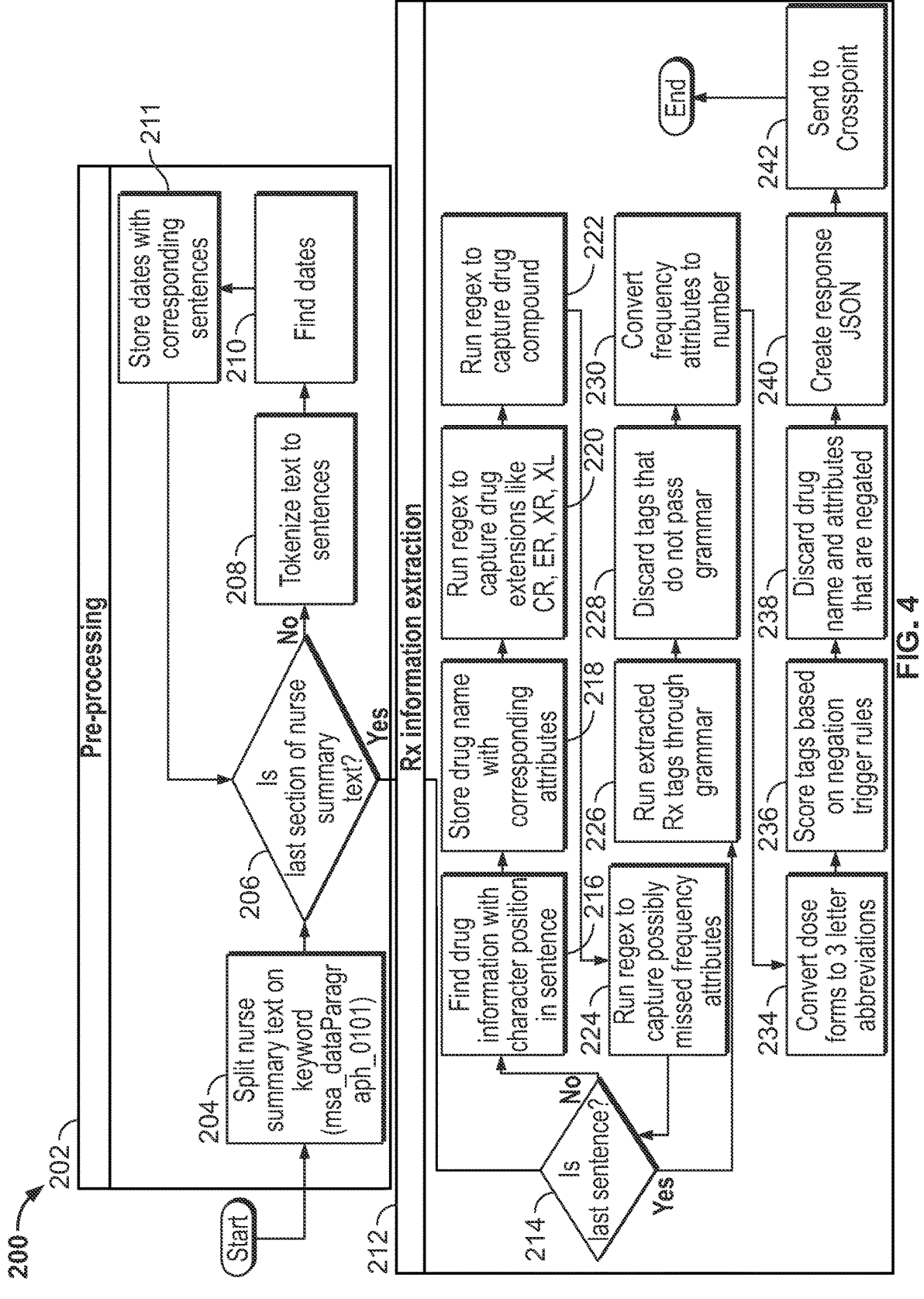
FIG. 4 is a flowchart illustrating processing steps carried out by the system of the present disclosure for extracting prescription information from nurse summary records using machine learning.

FIG. 4 is a flowchart illustrating processing steps, indicated generally at 200, carried out by the system of the present disclosure for extracting prescription information from nurse summary records using machine learning. A pre-processing phase 202 is first carried out, wherein in step 204, the system splits the nurse summary text on a keyword. Then, in step 206, a determination is made as to whether the last section of the nurse summary text is being processed. If so, a positive determination is made, wherein the system tokenizes the text into sentences. Then, in step 210, the system finds relevant dates. Next, in step 211, the system stores the dates with corresponding sentences, and control returns to step 206.

If a positive determination is made in step 206, a pre-scription ("Rx") information extraction process 212 is carried out. Beginning in step 214, a determination is made as to whether the last sentence of the nurse summary is identified. If a negative determination is made, step 216 occurs, wherein the system finds drug information with the character position in the sentence. Then, in step 218, the system stores the drug name with corresponding attributes. In step 220, the system runs a regular expression processing algorithm ("regex") to capture drug extensions (tags) such as CR, ER, XR, XL, etc. In step 222, the system runs the regex algorithm to capture the drug compound name (tags). In step 224, the system runs regex to capture possibly missed frequency attributes (tags). Control then returns to step 214.

If a positive determination is made in step 214, step 226 occurs, wherein the system runs the extracted prescription tags through a pre-defined grammar. Next, in step 228, the system discards tags that do not pass the grammar. In step 230, the system converts the frequency attributes to numbers. In step 234, the system converts dose forms (information) into 3-letter abbreviations. In step 236, the system scores the tags based on pre-defined negation trigger rules.

In step 238, the system discards drug names and attributes that are negated. In step 240, the system generates a JavaScript Object Notation (JSON) response that includes the aforementioned information, and in step 242, the system sends the JSON response to a data exchange platform.

Figure 5:
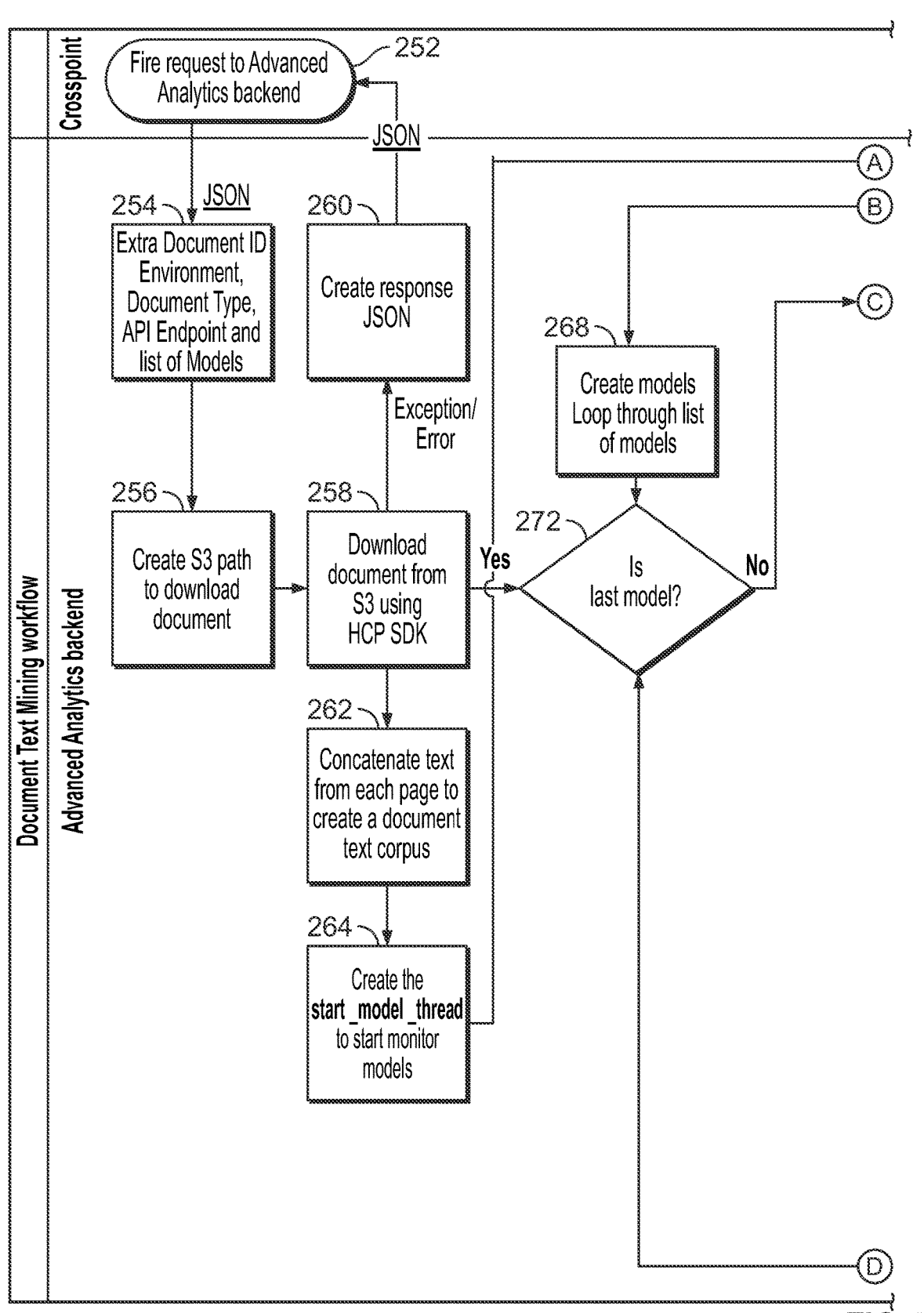
FIG. 5 is a flowchart illustrating processing steps carried out by the system for classification of sentences and tagging of terms in medical records using machine learning.
Figure 5:
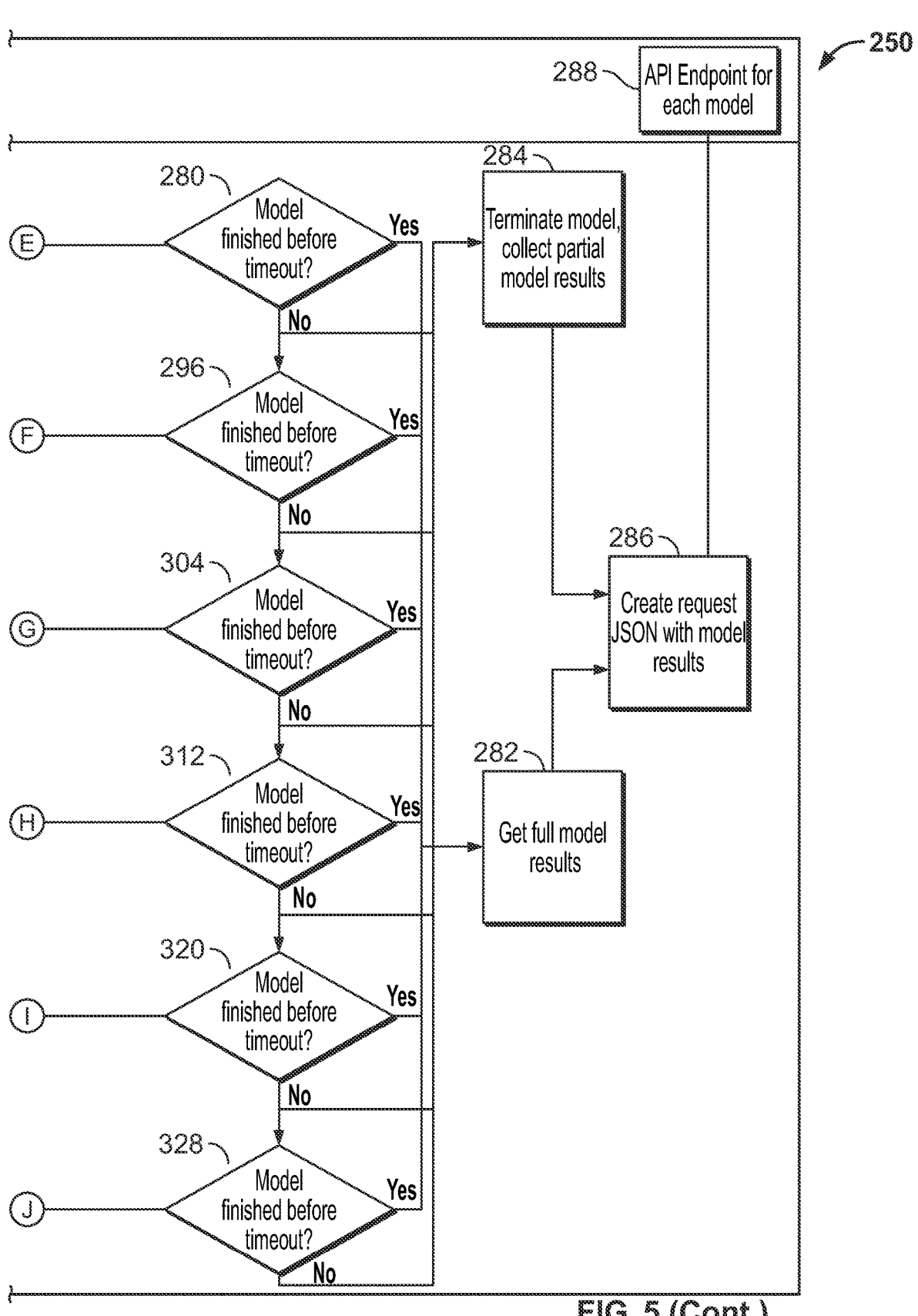

FIG. 5 is a flowchart illustrating processing steps, indicated generally at 250, carried out by the system for classification of sentences and tagging of terms in medical records using machine learning. In step 252, the system generates (fires) a request for advance analytics to be performed (e.g., by the analytics backend 48 of FIG. 2B). In step 254, the system extracts a document ID, environment document type, application programming interface ("API") endpoint, and a list of all models. In step 156, the system creates a cloud storage path (e.g., S3 storage path) to download the document. In step 258, the system downloads the document from the cloud storage path using a suitable content platform software development kit, such as the Hitachi Content Platform Software Development Kit ("HCP SDK"). Then, in step 260, the system creates and transmits a JSON response advising of the aforementioned activities.

In step 262, the system concatenates text from each page to create a document text corpus. In step 264, the system creates threads to start and monitor the models. In step 266, the system creates the model starting thread. In step 268, the system creates the models and loops through a list of models, and in step 270, the system monitors all currently-executing models. In step 272, a determination is made as to whether the last model has been identified. If not, step 274 occurs, wherein a determination is made as to whether the model is a sentence classification model. If so, step 276 occurs, wherein the system creates and starts a thread with timeout capabilities to process the document through a sentence classification model, and executes the model in step 278. In step 280, a determination is made as to whether the model has finished executing before the timeout. If so, step 282 occurs, wherein the full model results are gathered. Otherwise, step 284 occurs, wherein the system obtains the full model results. Otherwise, step 284 occurs, wherein the system terminates the model and collects partial model results. In step 286, the system creates a JSON request that includes the model results, and in step 288 the system makes the model results available using an API endpoint for each model.

In step 290, the system determines whether the model is a comorbidity model. If so, step 292 occurs, wherein the system creates and starts a thread with a timeout parameter to process the document through the comorbidity model. In step 294, the system executes a comorbidity tagging process, using the model to identify (tag) each comorbidity present in the document. In step 296, the system determines whether the model has finished executing before the timeout. If a positive determination is made, step 282 occurs; otherwise, step 284 occurs.

In step 298, the system determines whether the model is an ICD model. If so, step 300 occurs, wherein the system creates and starts a thread with a timeout parameter to process the document through the ICD model. In step 302, the system executes an ICD tagging process, using the model to identify (tag) each ICD code present in the document. In step 304, the system determines whether the model has finished executing before the timeout. If a positive determination is made, step 282 occurs; otherwise, step 284 occurs.

In step 306, the system determines whether the model is a body parts model. If so, step 308 occurs, wherein the system creates and starts a thread with a timeout parameter to process the document through the body parts model. In step 310, the system executes an ICD tagging process, using the model to identify (tag) each ICD code present in the document. In step 312, the system determines whether the model has finished executing before the timeout. If a positive determination is made, step 282 occurs; otherwise, step 284 occurs.

In step 314, the system determines whether the model is a prescription model. If so, step 316 occurs, wherein the system creates and starts a thread with a timeout parameter to process the document through the prescription model. In step 318, the system executes a prescription tagging process, using the model to identify (tag) each prescription present in the document. In step 320, the system determines whether the model has finished executing before the timeout. If a positive determination is made, step 282 occurs; otherwise, step 284 occurs.

In step 322, the system determines whether the model is a provider name model. If so, step 324 occurs, wherein the system creates and starts a thread with a timeout parameter to process the document through the provider name model. In step 326, the system executes a provider name tagging process, using the model to identify (tag) each provider name present in the document. In step 328, the system determines whether the model has finished executing before the timeout. If a positive determination is made, step 282 occurs; otherwise, step 284 occurs.

Advantageously, the processing steps 250 of FIG. 5 allow multiple models to execute independently and in parallel, including the sentence classification model, the comorbidity model, the ICD model, the body parts model, the prescription model, and the provider name model, using a dedicated computer processing thread allocated to each model. This significantly increases the speed with which the system can process a document to identify relevant information using multi-threaded, machine learning models. Additionally, by collecting all of the modeling results and delivering same in a customized, unified API endpoint for each model, the system greatly increases the speed and ease with which modeling results can be accessed by users and/or computing resources.

Figure 6:
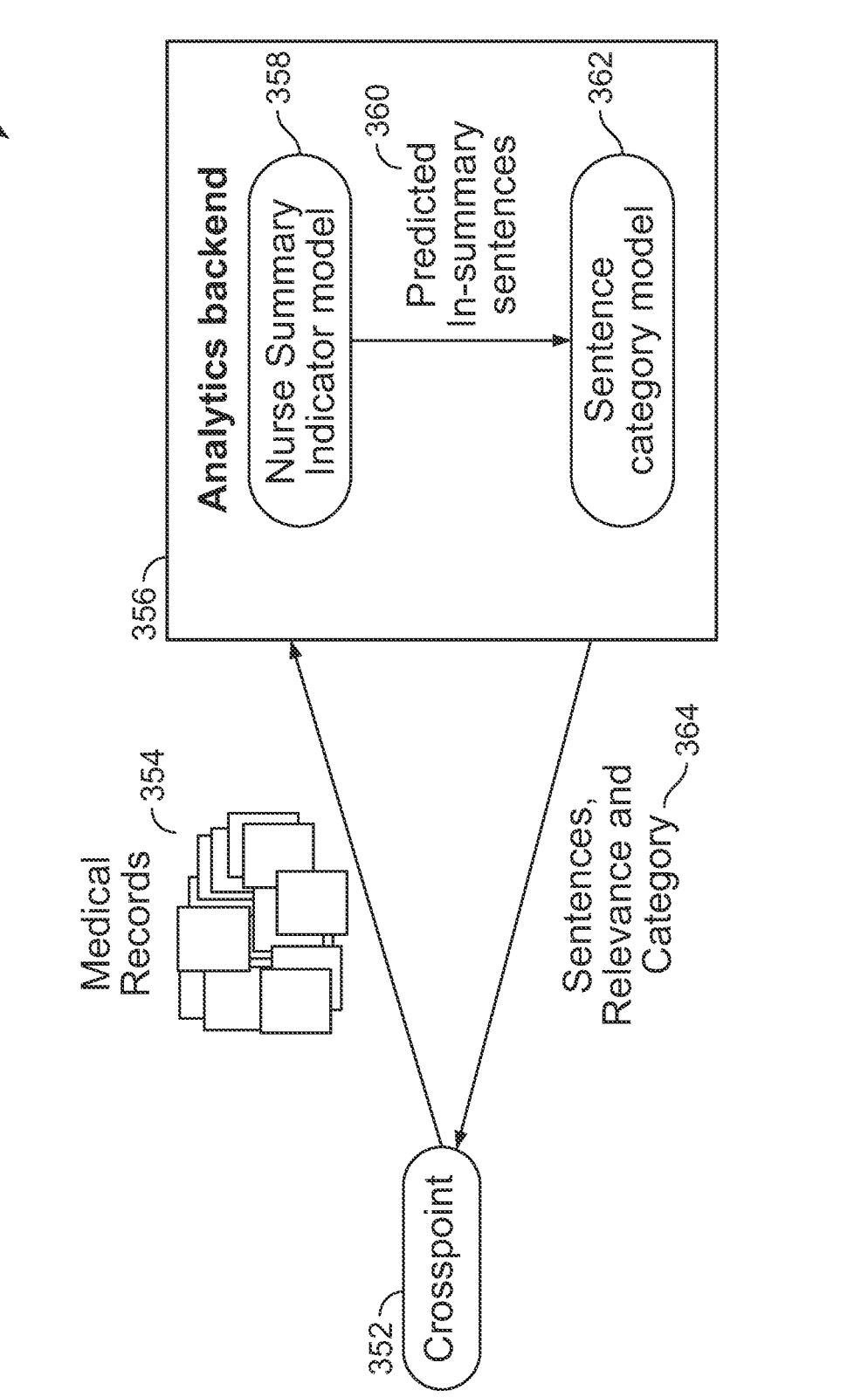
FIG. 6 is a diagram illustrating sentence classification processes carried out by the system of the present disclosure.

FIG. 6 is a diagram illustrating sentence classification processes carried out by the system of the present disclosure, indicated generally at 350. As can be seen, the system retrieves medical records 354 from a data source, such as a data exchange platform 352. The records 354 can be processed by an analytics backend 356 to identify sentences, relevance, and category information from the records 354 and deliver the results to the data platform 352. The backend 356 can execute a nurse summary indicator model 358 which predicts in-summary sentences 360 from nurse records, and a sentence category model 362.

Figure 7:
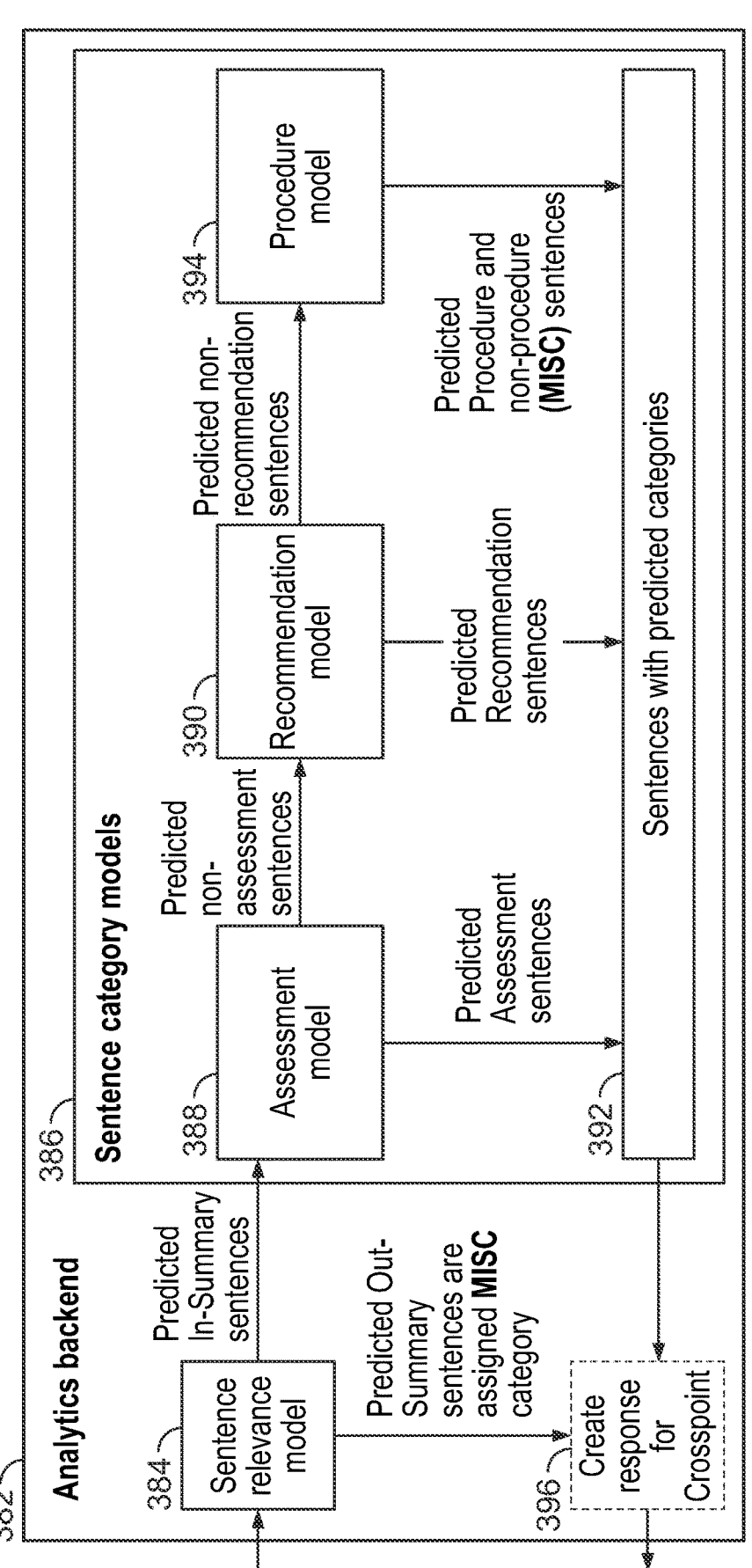
FIG. 7 is a diagram illustrating the architecture of the analytics backend of FIG. 6, for sentence classification using machine learning.

FIG. 7 is a diagram illustrating the architecture 380 of the analytics backend of FIG. 6, for sentence classification using machine learning. The analytics backend 382 (which could correspond to the backend 356 of FIG. 6) includes a sentence relevance model 384 that processes nurse records to predict in-summary sentences as well as to predict out-summary sentences which are assigned a miscellaneous category. One or more sentence category models 386 process the predicted in-summary sentences to generate sentences with predicted categories 392, which could be provided for use by a data exchange platform in process 396. The models 386 could include, but are not limited to, an assessment model 388 (which predicts assessment and non-assessment sentences 388), a recommendation model 390 (which predicts recommendation and non-recommendation sentences), and a procedure model 394 (which predicts procedure and non-procedure (miscellaneous) sentences).

Figure 8:
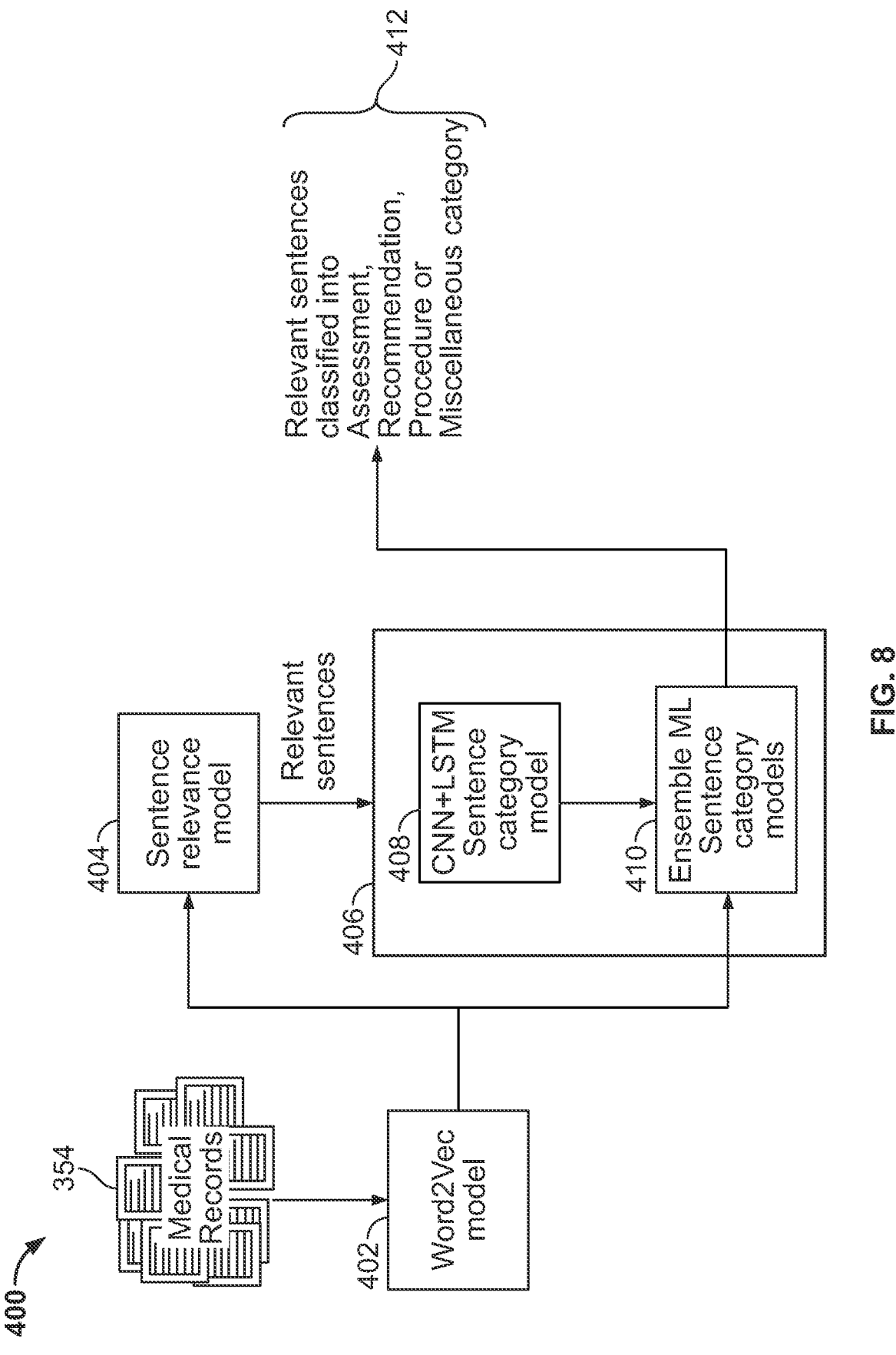
FIG. 8 is a diagram illustrating training by the system of sentence classification models.

FIG. 8 is a diagram illustrating training by the system of sentence classification models, indicated generally at 400. The medical records 354 are processed by one or more word to vector (word2vec) models 402 to create vectors from words of the medical records 354, which are fed to a sentence relevance model 404 and a hybrid model 406 which includes a convolutional neural network and long short-term model (CNN+LSTM) 408 and ensemble machine learning (ML) sentence category models 410. The models 410 generate output data 412 which includes, but is not limited to, relevant sentences classified into assessments, recommendations, procedures, or miscellaneous categories.

Figure 9:
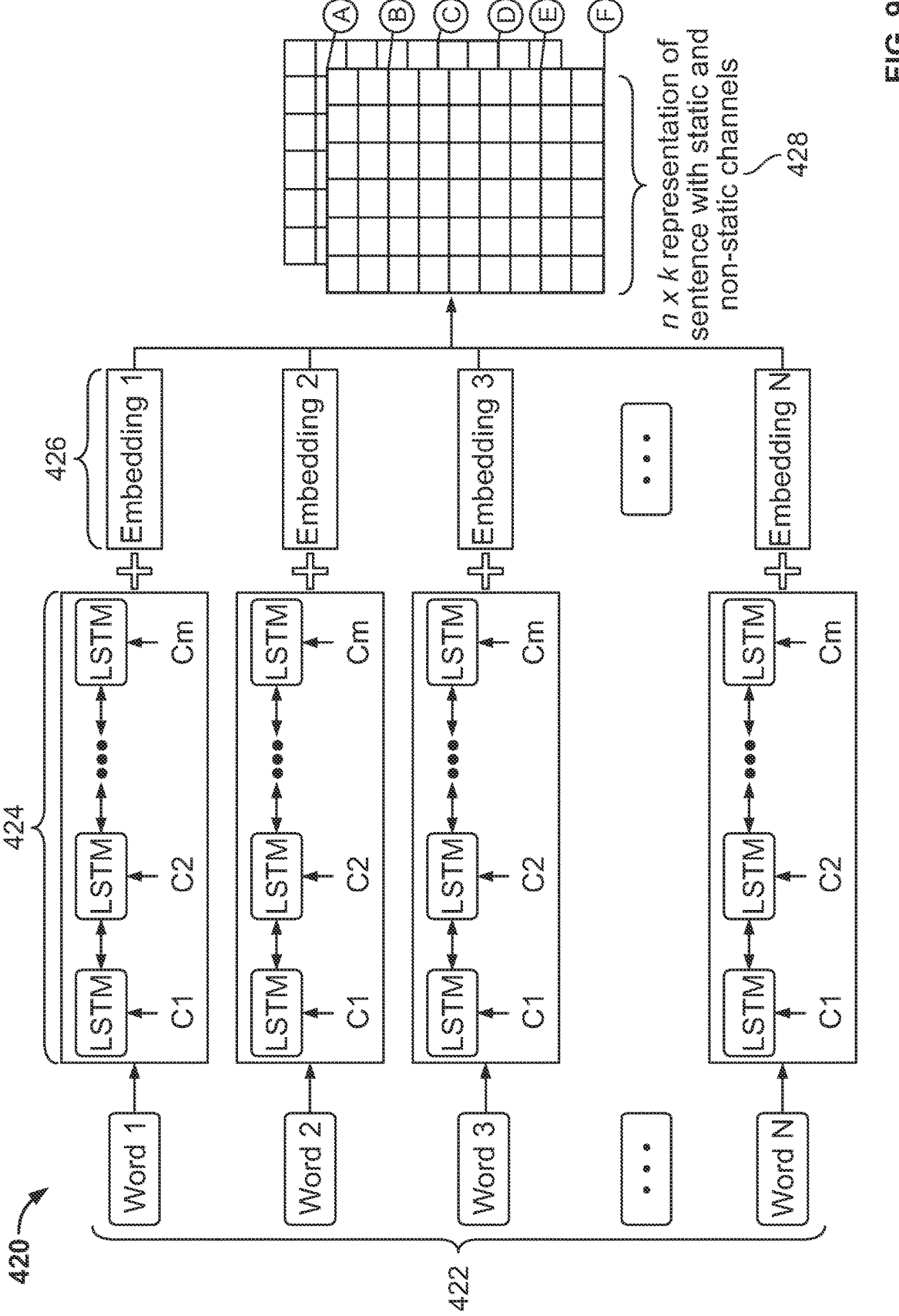
FIG. 9 is a diagram illustrating a deep neural network structure implemented by the system of the present disclosure for sentence classification from medical data using machine learning.
Figure 9:
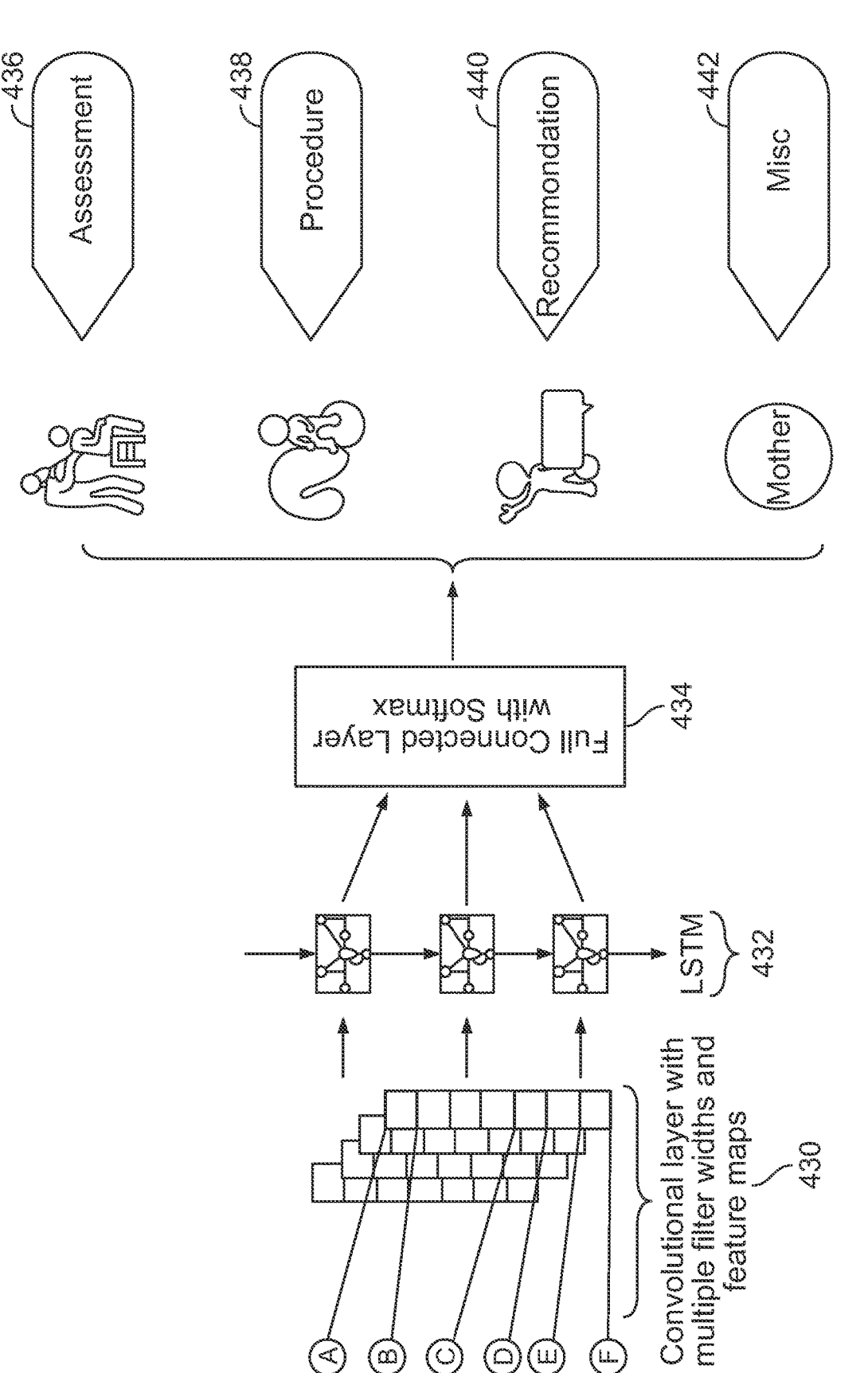

FIG. 9 is a diagram illustrating a deep neural network structure 420 implemented by the system of the present disclosure for sentence classification from medical data using machine learning. The network 420 takes as input a plurality of words 422 from the medical records, and processes the words using chained LSTM models in step 424. In step 426, embeddings are added to the outputs of the LSTM models, and the results are transformed into n×k representations 428 of sentences having static and non-static channels. In step 430, the n×k representations 428 are processed by the system to generate one or more convolutional neural network layers with multiple filter widths and feature maps. The CNN layers are then processed by a plurality of LSTMs 432 to generate a full convolution layer 432 with softmax features. The layer 432 then generates outputs that the machine has learned from the data, including learned assessment features 436, learned procedures 458, recommendations 440, and miscellaneous data 442.

Figure 10:
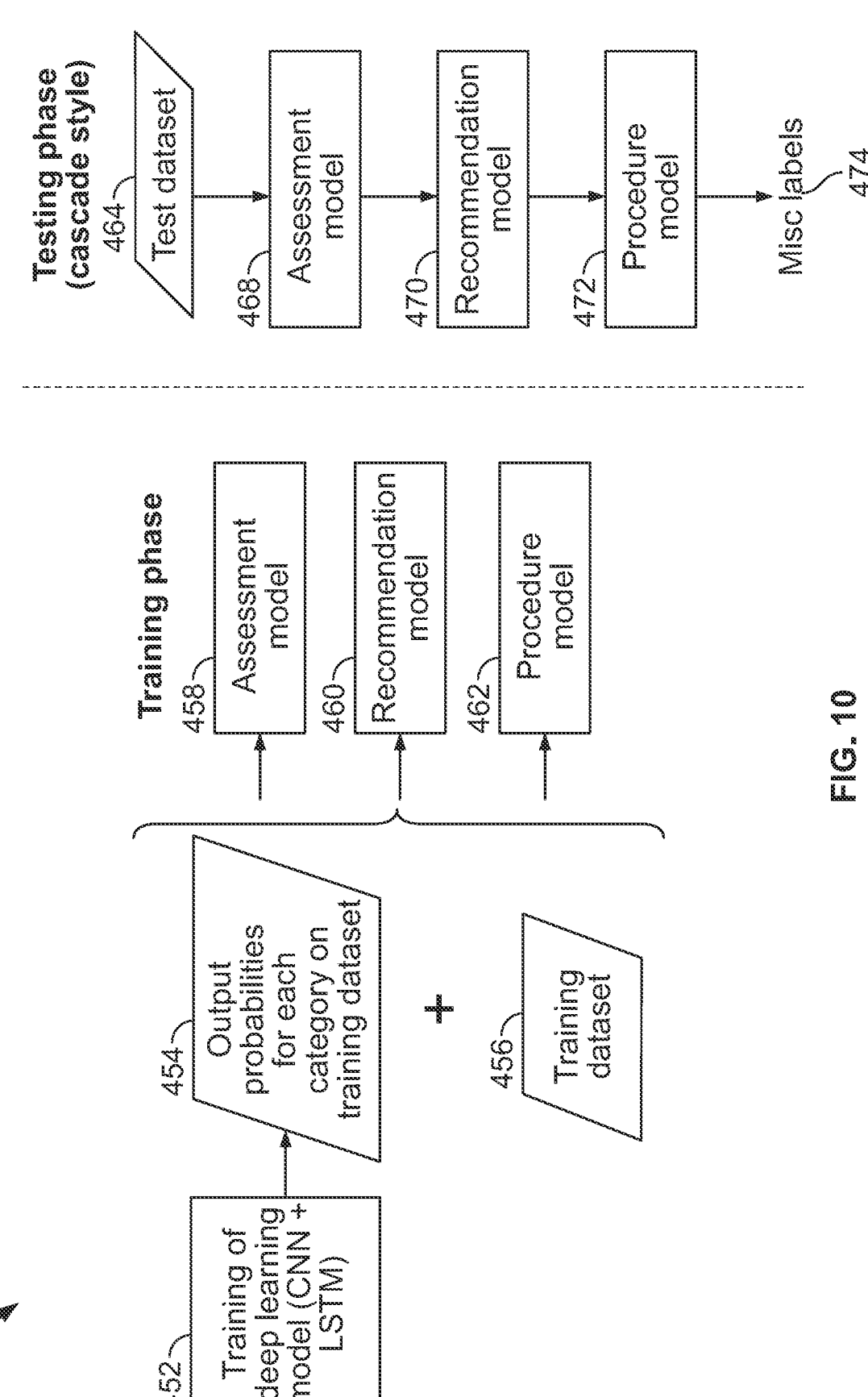
FIG. 10 is a diagram illustrating an integrated deep learning model for sentence classification implemented by the system of the present disclosure.

FIG. 10 is a diagram 450 illustrating an integrated deep learning model for sentence classification implemented by the system of the present disclosure. In step 452, the system trains the deep learning models (including the CNN and LSTM models discussed above). In step 434, the system outputs probabilities for each category of the training dataset 456. Then, an assessment model 458, a recommendation model 460, and a procedure model 462 are trained using the output probabilities 434 and training dataset 456. Once training is complete, a testing phase occurs, wherein a test dataset 464 is processed using the trained assessment model 468, the trained recommendation model 470, and the trained procedure model 472, generating assessment, recommendation, procedure, and miscellaneous labels 474 for sentences that can be evaluated to determine the effectiveness of the training phase.

Figure 11:
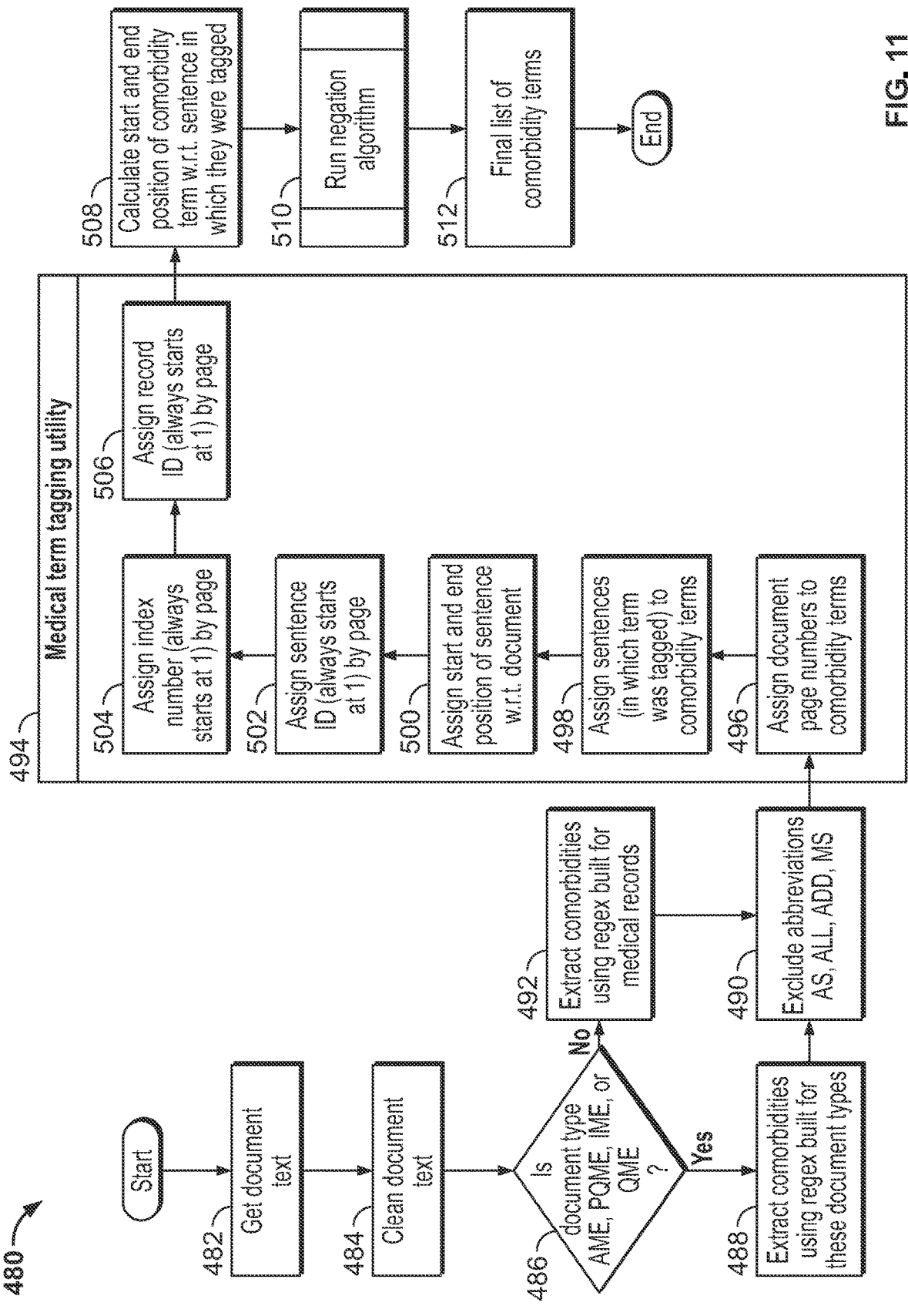
FIG. 11 is a flowchart illustrating machine learning processes carried out by the system of the present disclosure for tagging of comorbidity data from medical records.

FIG. 11 is a flowchart illustrating machine learning processes carried out by the system of the present disclosure for tagging of comorbidity data from medical records, indicated generally at 480. In step 482, the system retrieves document text (e.g., from the medical records, or from OCR applied to one or more scanned documents). In step 484, the system cleans the document text. In step 486, the system determines whether the document type is Agreed Medical Exam ("AME"), Panel Qualified Medical Examination ("PQME"), Independent Medical Examination ("IME"), or Qualified Medical Examination ("QME"). If a positive determination is made, step 488 occurs, wherein the system extracts comorbidities using the regex algorithm built for each of the document types. Then, in step 490, all, or a subset of, the abbreviations are excluded in order to reduce tagging errors in the model. For examples, abbreviations of AS, ALL, ADD, and MS corresponding to comorbidity terms can be excluded, if desired. Otherwise, in step 492, the system extracts comorbidities using the regex algorithm built for medical records, and step 490 occurs.

In process 494, medical tagging occurs. In step 496, the system assigns document page numbers to the comorbidity terms. In step 498, the system assigns sentences (in which the term was tagged) to the comorbidity terms. In step 500, the system assigns start and end positions of each sentence with respect to the document. In step 502, the system assigns sentence IDs by page. In step 504, the system assigns index numbers by page. In step 506, the system assigns record IDs by page. In step 508, the system calculates start and end positions of comorbidity terms with respect to the sentence in which they were tagged. In step 510, the system runs a negation algorithm on the data. Finally, in step 512, the system generates a final list of comorbidity terms.

Figure 12:
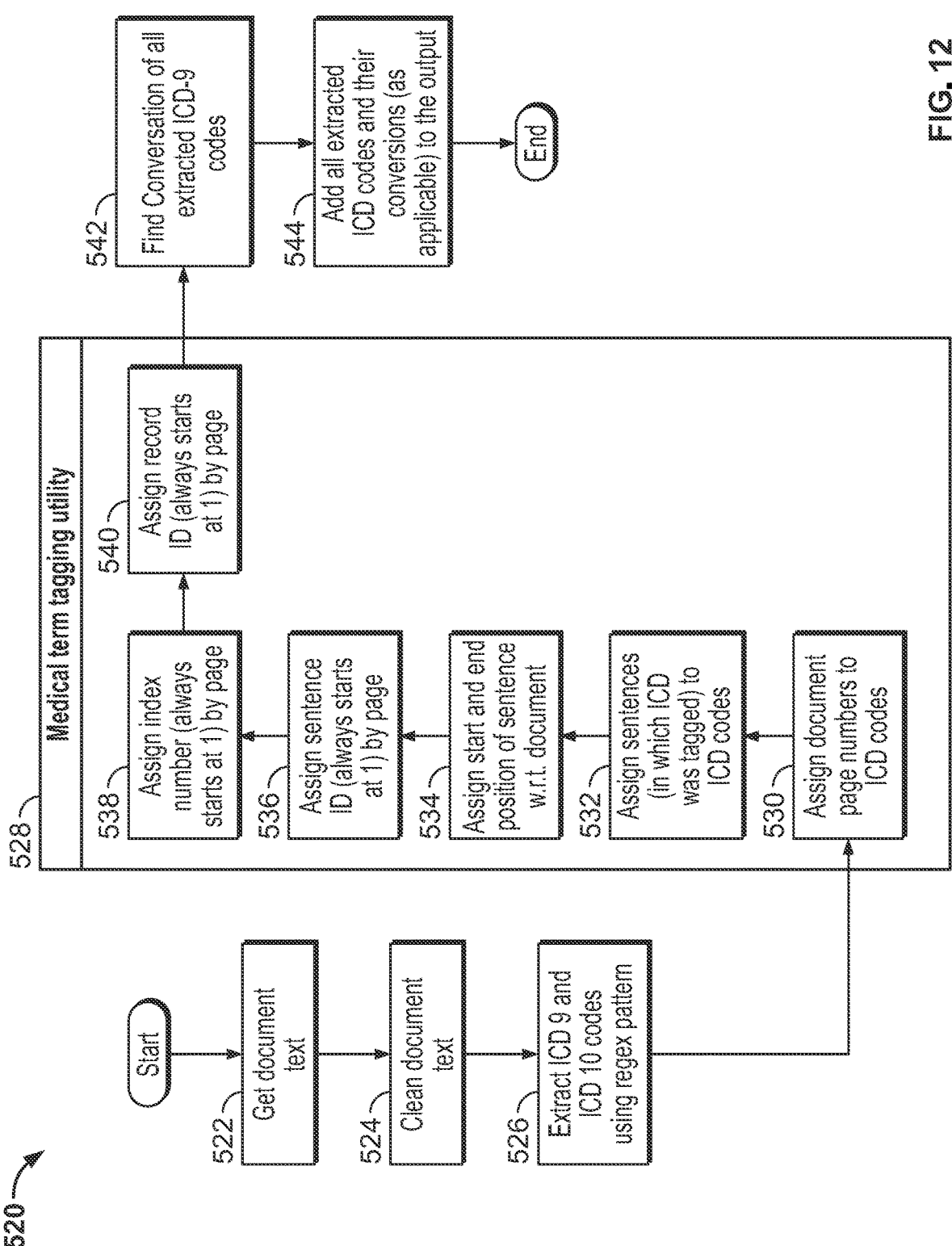
FIG. 12 is a flowchart illustrating machine learning processes carried out by the system of the present disclosure for tagging of diagnosis and ICD code data from medical records.

FIG. 12 is a flowchart illustrating machine learning processes carried out by the system of the present disclosure for tagging of diagnosis and ICD code data from medical records, indicated generally at 520. In step 522, the system retrieves document text (e.g., from the medical records, or from OCR applied to one or more scanned documents). In step 524, the system cleans the document text. In step 526, the system extracts ICD 9 and ICD 10 codes using a regex pattern.

In process 528, medical tagging occurs. In step 530, the system assigns document page numbers to the ICD codes. In step 532, the system assigns sentences (in which the term was tagged) to the ICD codes. In step 534, the system assigns start and end positions of each sentence with respect to the document. In step 536, the system assigns sentence IDs by page. In step 538, the system assigns index numbers by page. In step 540, the system assigns record IDs by page. In step 542, the system finds conversions of all extracted ICD-9 codes. Finally, in step 544, the system adds all extracted ICD codes and their conversions to the output.

Figure 13:
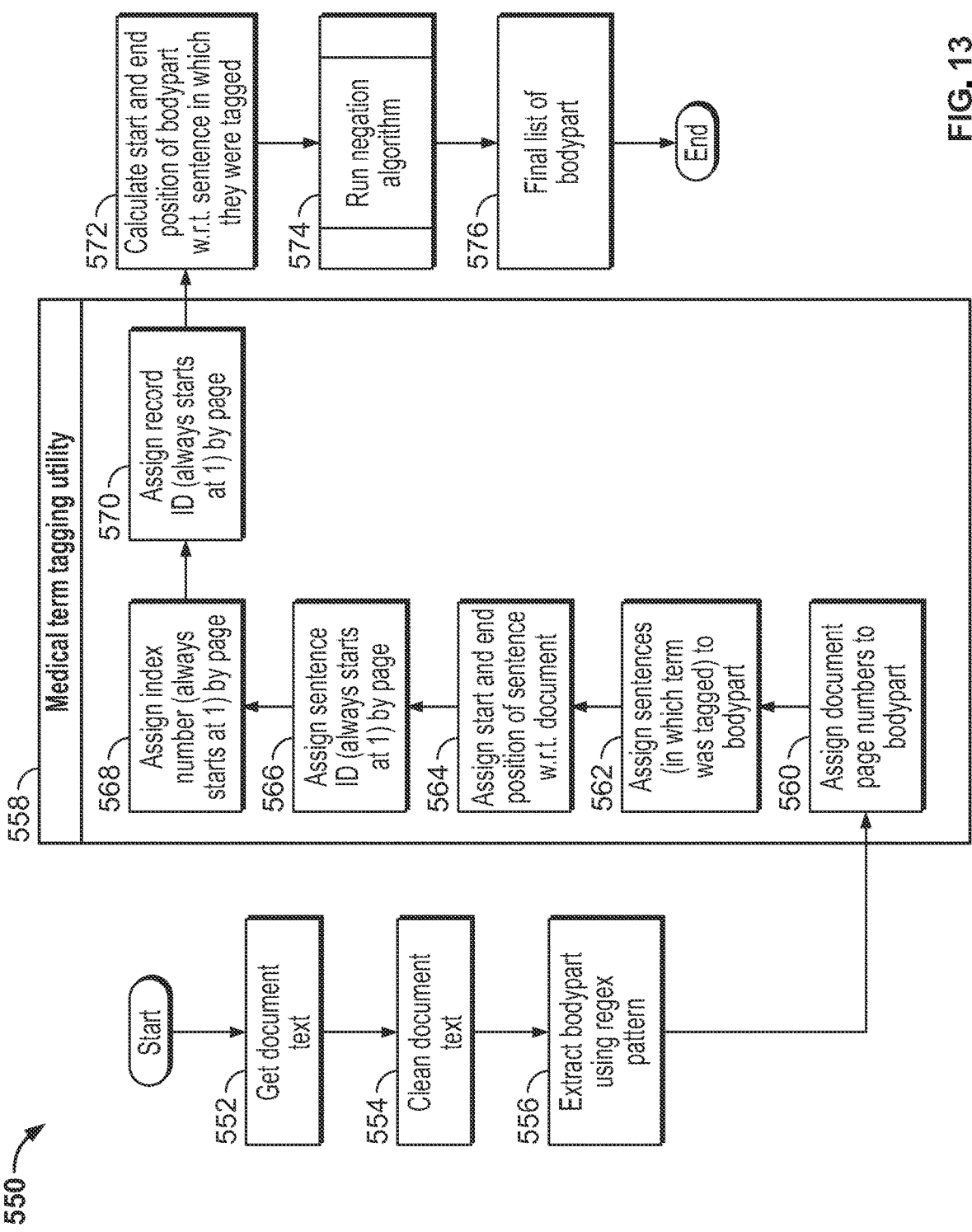
FIG. 13 is a flowchart illustrating machine learning processes carried out by the system of the present disclosure for tagging body part data from medical records.

FIG. 13 is a flowchart illustrating machine learning processes carried out by the system of the present disclosure for tagging body part data from medical records, indicated generally at 550. In step 552, the system retrieves document text (e.g., from the medical records, or from OCR applied to one or more scanned documents). In step 554, the system cleans the document text. In step 556, the system extracts body part terms using the regex pattern.

In process 558, medical tagging occurs. In step 560, the system assigns document page numbers to the body part terms. In step 562, the system assigns sentences (in which the term was tagged) to the body part terms. In step 564, the system assigns start and end positions of each sentence with respect to the document. In step 566, the system assigns sentence IDs by page. In step 568, the system assigns index numbers by page. In step 570, the system assigns record IDs by page. In step 572, the system calculates start and end positions of body part terms with respect to the sentence in which they were tagged. In step 574, the system runs a negation algorithm on the data. Finally, in step 576, the system generates a final list of body part terms.

Figure 14:
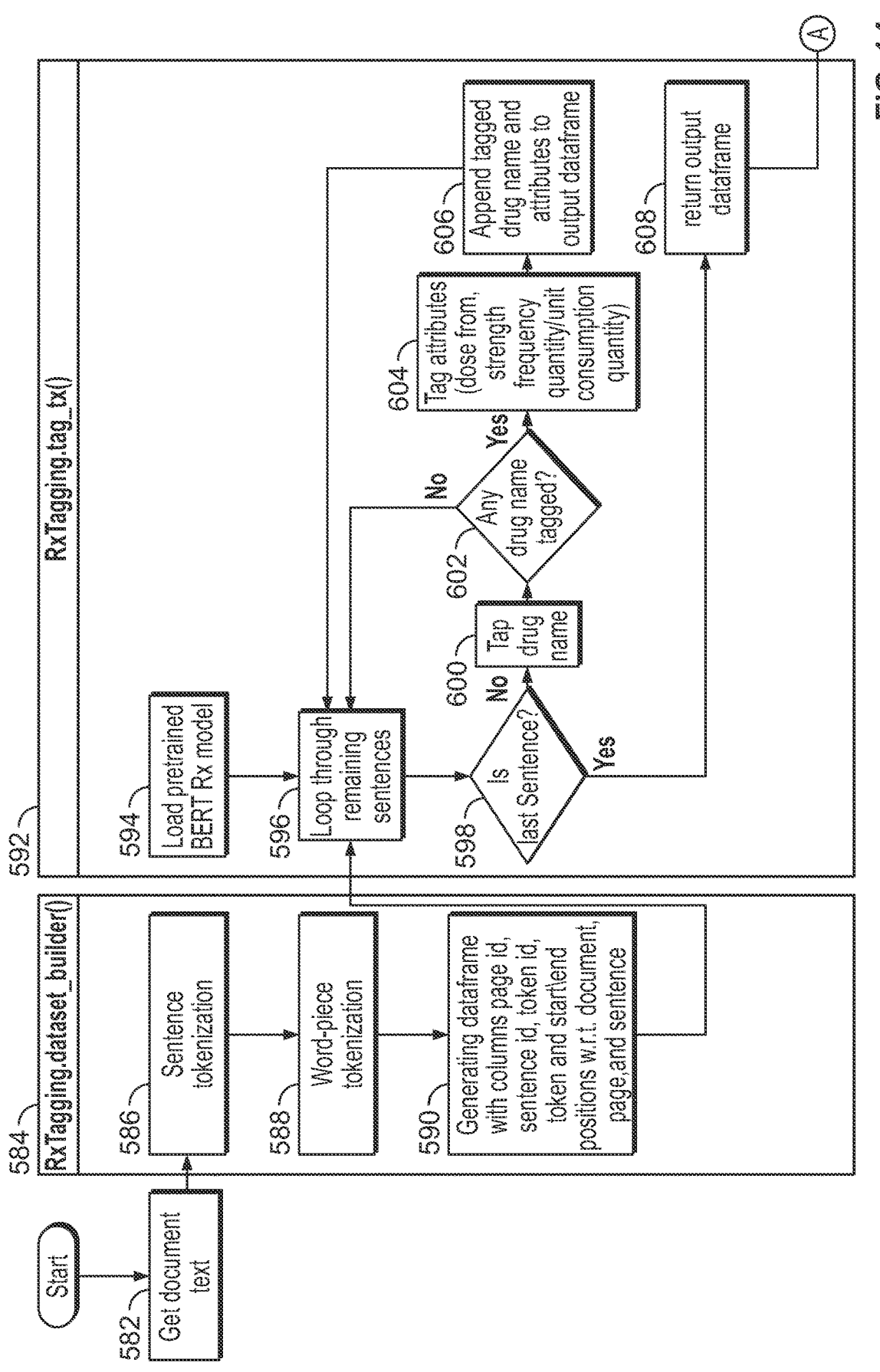
FIG. 14 is a flowchart illustrating machine learning processes carried out by the system of the present disclosure for tagging of prescriptions from medical records.
Figure 14:
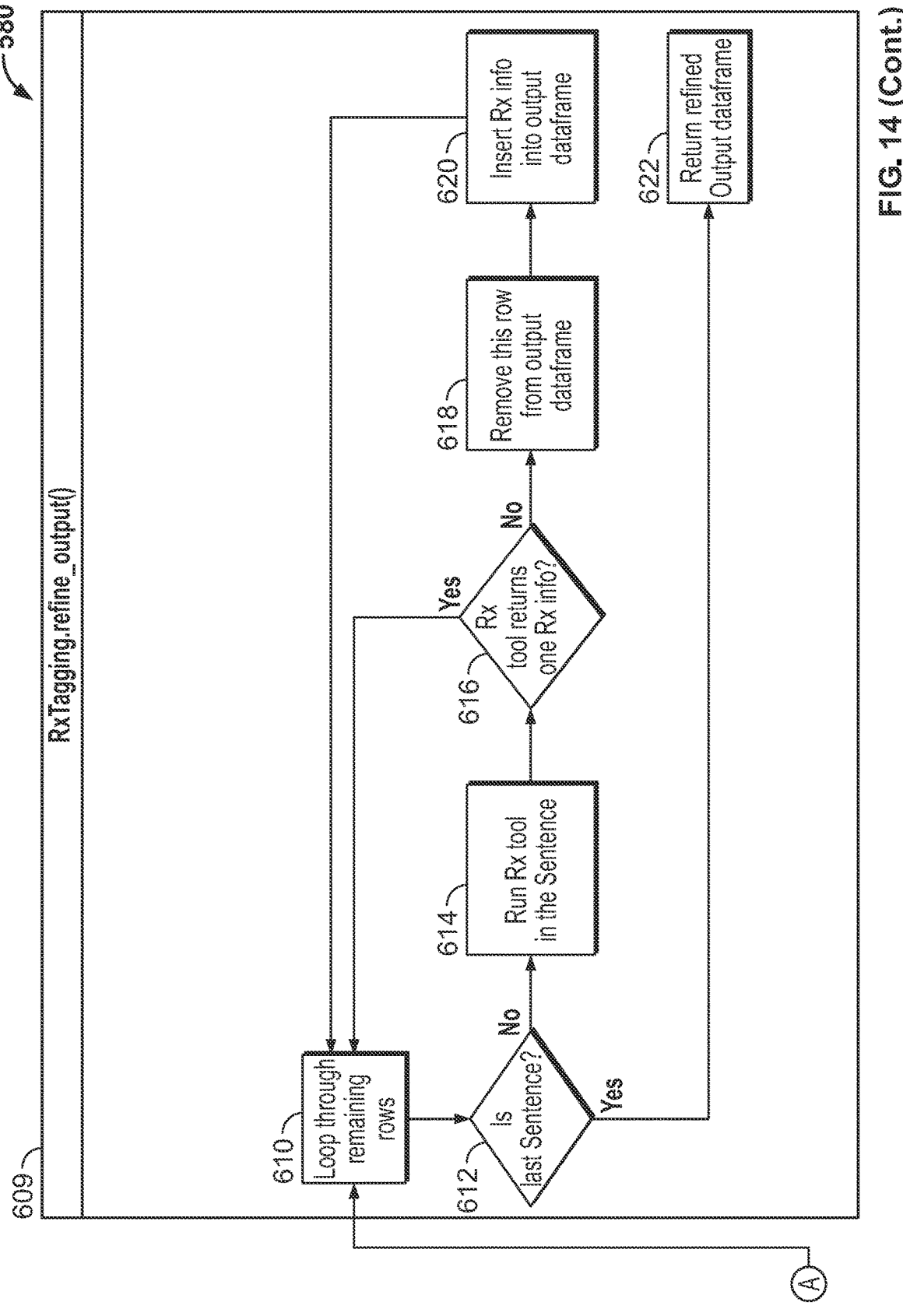

FIG. 14 is a flowchart illustrating machine learning processes carried out by the system of the present disclosure for tagging of prescriptions from medical records, indicated generally at 580. In step 582, the system obtains document text (e.g., from the medical records, or from OCR applied to one or more scanned documents). Then, a dataset builder process 584 is performed on the document text, including sentence tokenization in step 586, word piece tokenization in step 588, and dataframe generation step 590 (using columns such as page identifier, sentence identifier, token identifier, tokens, start and end positions with respect to document page, and sentence information).

Next, prescription tagging process 592 is carried out. In step 594, the pre-trained prescription model is loaded by the system. Then, in step 596, the system loops through the remaining sentences. In step 598, a decision is made as to whether the last sentence is reached. If so, step 608 occurs, wherein the system returns the output data frame. Otherwise, step 600 occurs, wherein the system tags the drug name. In step 602, a determination is made as to whether any drug names are tagged. If not, control returns to step 596. Otherwise, step 604 occurs, wherein the system tags attributes such as the dose form, strength, frequency, quantity, unit, consumption quantity, and other information. In step 606, the system appends the tagged drug name and attributes to the output data frame and control returns to step 596.

Finally, a tagging refinement process 609 occurs. In step 610, the system loops through remaining rows of the data set. In step 612, a determination is made as to whether the last sentence is encountered. If so, step 622 occurs, wherein the system returns the refined output data frame. Otherwise, step 614 occurs, wherein the system runs the prescription tool in the sentence. Then, in step 616, a determination is made as to whether the prescription tool returns one prescription item of information. If so, control returns to step 610. If not, step 618 occurs, wherein the system removes the current row from the output data frame. Then, in step 620, the system inserts the prescription information into the output data frame.

FIG. 15 is a flowchart illustrating machine learning processes carried out by the system of the present disclosure for determining a prescription payment history from medical records, indicated generally at 630. In step 632, the system receives a JSON request. In step 634, the system parses the payment history data from the JSON request. In step 636, the system passes sentences through a dictionary to find prescription information. In step 638, the system uses company and/or client specific regex patterns that match to put the extracted information into the correct format. In step 640, the system executes logic for each company and/or client to discard mis-tagged information. In step 642, the system checks the dictionary for any alias drug names and updates them. In step 644, the system creates a response JSON with the prescription results. Finally, in step 646, the system transmits the response JSON to a data exchange platform.

Figure 16:
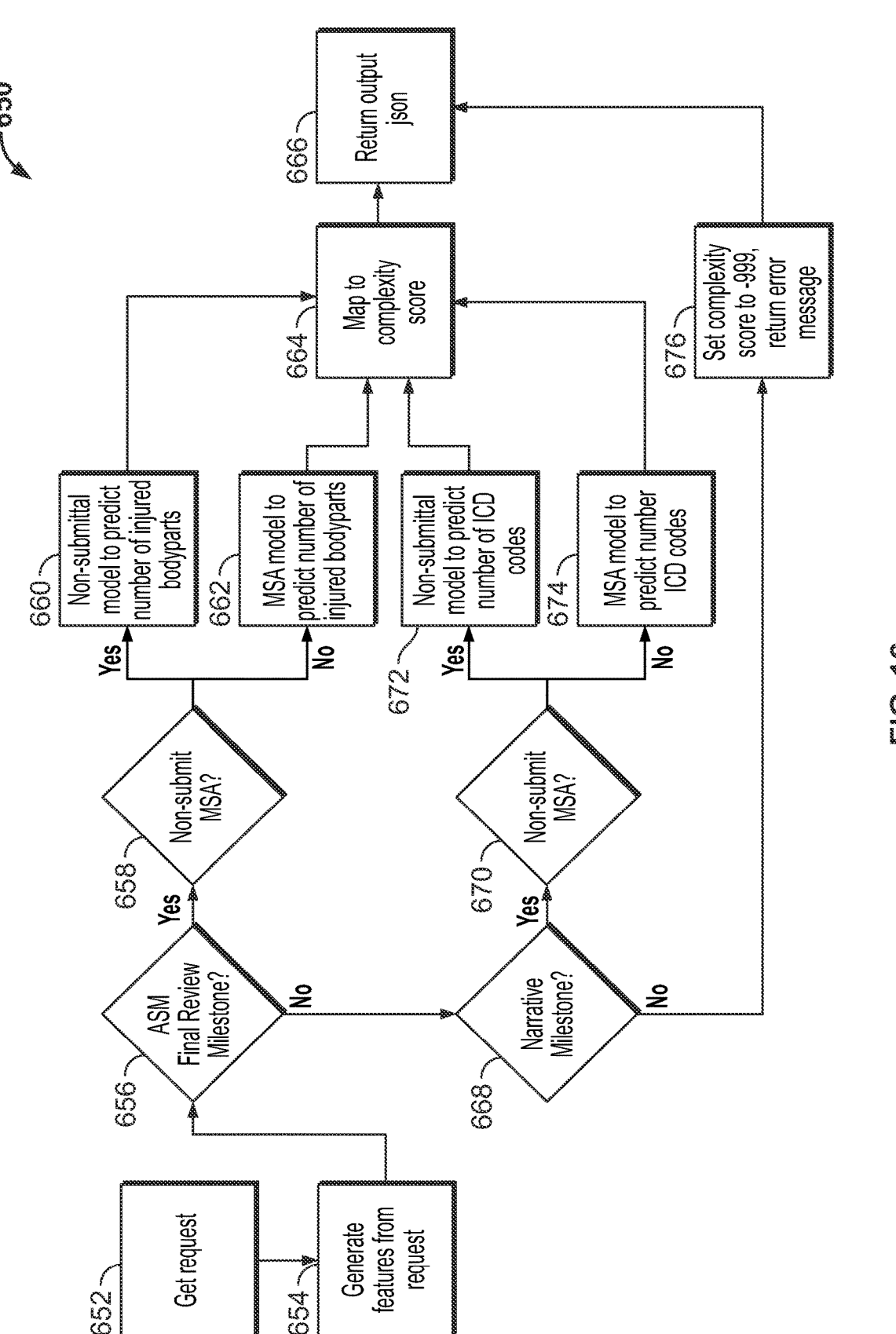
FIG. 16 is a flowchart illustrating machine learning processes carried out by the system of the present disclosure for scoring the complexity of a medical claim.

FIG. 16 is a flowchart illustrating machine learning processes carried out by the system of the present disclosure for scoring the complexity of a medical claim, indicated generally at 650. In step 652, the system receives a request, and in step 654, the system generates features from the request. In step 656, the system determines whether an account services manager ("ASM") final review milestone has occurred. If so, step 658 occurs, wherein the system determines whether the MSA should not be submitted. If so, step 660 occurs, wherein a non-submittal model is utilized to predict the number injured body parts. Otherwise, step 662 occurs, wherein the MSA model is utilized to predict the number of injured body parts. In step 664, the system maps the complexity score, and in step 666, the system returns output (e.g., in the form of a JSON response).

In the event that a negative determination is made in step 656, step 668 occurs, wherein the system determines whether a narrative milestone has been reached. If so, step 670 occurs, wherein the system determines whether the MSA should not be submitted. If so, step 672 occurs, wherein the a non-submittal model is utilized to predict the number of ICD codes, and control passes to step 664.

Otherwise, step 674 occurs, wherein an MSA model is used to predict the number of ICD codes, and control passes to step 664. In the even that a negative determination is made in step 668, step 676 occurs, wherein the system sets the complexity score to a pre-set value (e.g., −999) and an error message is returned and control is passed to step 666.

Figure 17:
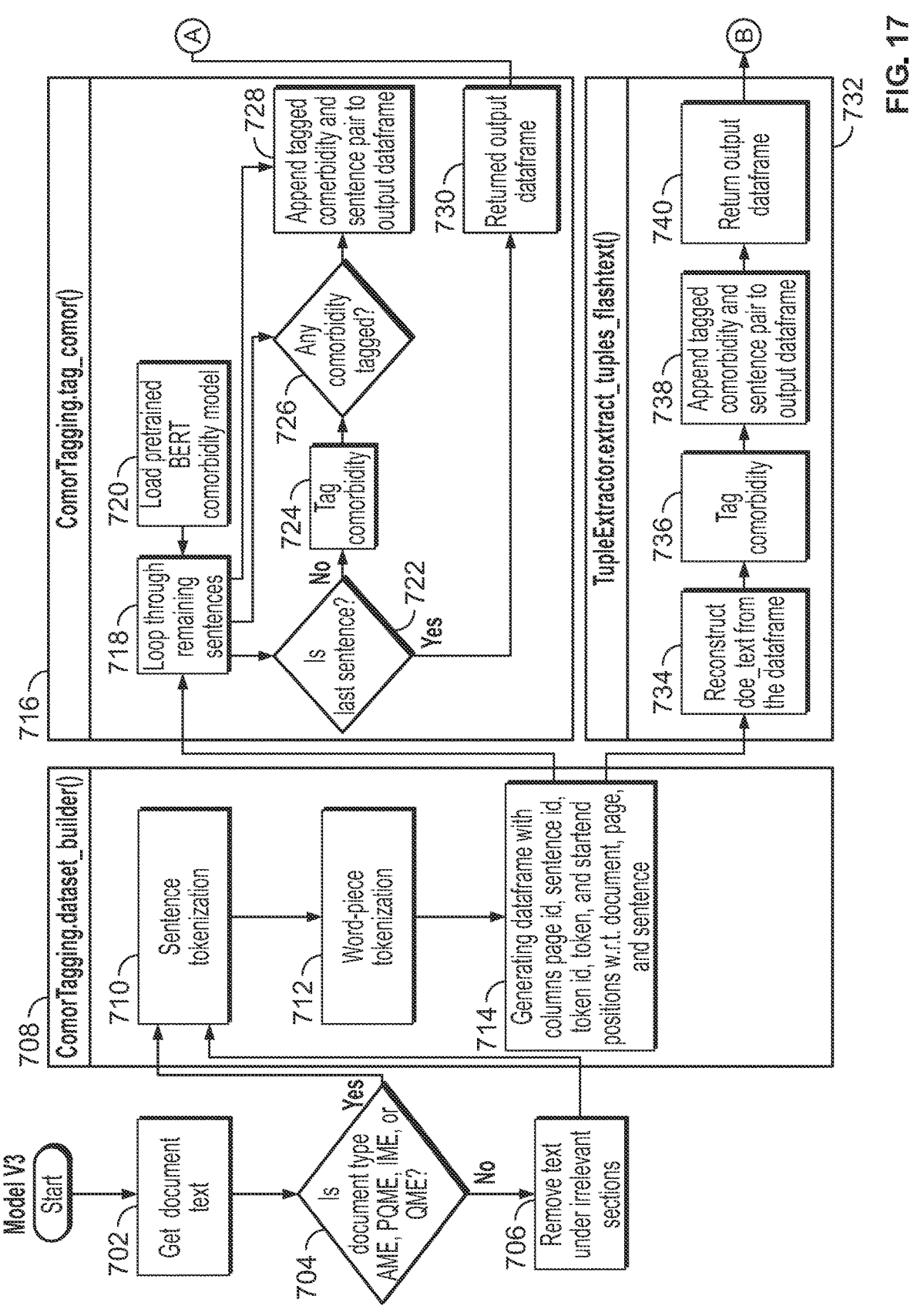
FIG. 17 is a flowchart illustrating another embodiment of the systems and methods of the present disclosure, wherein improved accuracy of extraction of comorbidity of data is provided.
Figure 17:
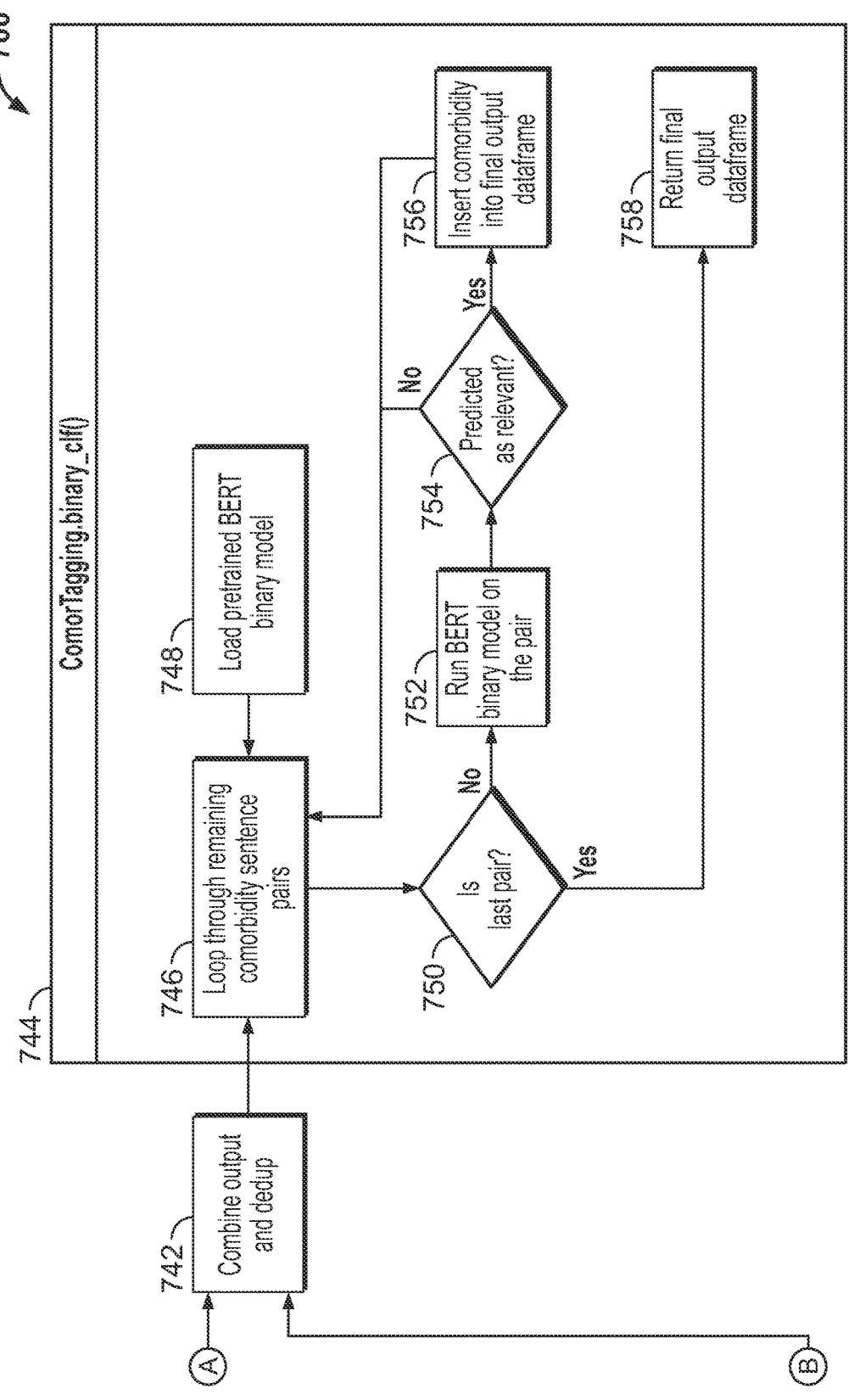

FIG. 17 is a flowchart illustrating another embodiment of the systems and methods of the present disclosure, indicate generally at 700, wherein improved accuracy of extraction of comorbidity of data is provided. In one aspect, a two-step model identifies every comorbidity term and determines if the comorbidity is relevant to the patient from the context of the medical records. In another aspect, the two-step model learns domain-specific contextual embeddings from a larger number of medical records during the model training process. Beginning in step 702, the system obtains text from a document such as a medical record. In step 704, a determination is made as to whether the document type corresponds to an Agreed Medical Exam (AME), a Panel Qualified Medical Examination (PQME), and Independent Medical Examination (IME), or a Qualified Medical Examination (QME) document type. If a negative determination is made, step 706 occurs, wherein the system removes text from irrelevant sections of the document. Otherwise, process 708 occurs, wherein the system generates a dataset from the document. Specifically, in step 710, the system tokenizes sentences in the document. Then, in step 712, the system processes the tokenized sentences to perform word-piece tokenization to identify specific words in the sentences. In step 714, the system generates a data frame that includes columns corresponding to a page identified (page_id), a sentence identifier (sentence_id), a token identifier (token_id), a token, and identification of the starting and ending positions of each word-piece with respect to the document, page, and sentence.

Upon completion of process 708, processes 716 and 732 occur. In process 716, the system tags comorbidities in the data frame. Specifically, in step 718, the system loops through remaining sentences in the data set, processing each sentence. In step 720, the system loads a pre-trained Bidirectional Encoder Representations from Transformers (BERT) comorbidity model, which is a transformer based deep learning natural language understanding model adapted for use with medical documents and comorbidity target labels. In step 722, the system determines whether the last sentence of the data frame has been processed. If so, step 730 occurs, wherein the system returns an output data frame. Otherwise, step 724 occurs, wherein the system tags comorbidities in the current sentence. Then, in step 726, a determination is made as to whether any comorbidities have been tagged. If a negative determination is made, control returns to step 718 so that the next sentence in the data frame can be processed. Otherwise, step 728 occurs, wherein the system appends the tagged comorbidity and sentence pair to the output data frame.

In process 732, the system extracts tuples from the data frame. Specifically, in step 734, the system reconstructs document text (doc_text) from the data frame. Then, in step 736, the system tags comorbidities in the document text. Next, in step 738, the system appends tagged comorbidities and sentence pairs to the output data frame. Then, in step 740, the system returns the output data frame.

In step 742, the system combines the output data frames and removes duplicates from (dedupes) the combined data frames. Next, process 744 occurs, wherein the system performs further tagging steps. Specifically, in step 746, the system loops through remaining comorbidity sentence pairs in the combined data frame, and in step 748, the system loads a pre-trained BERT binary model. In step 750, a determination is made as to whether the last pair of the combined data frames has been reached. If so, step 758 occurs, wherein the system returns the final output data frame. Otherwise, step 752 occurs, wherein the system runs the BERT binary model on the current pair. Then, in step 754, the system determines whether the BERT model predicts the current pair as relevant to a comorbidity issue. If not, control returns to step 746 so that the next pair of the combined data frames can be processed. Otherwise, step 756 occurs, wherein the system inserts the detected comorbidities into the final output data frame.

Figure 18:
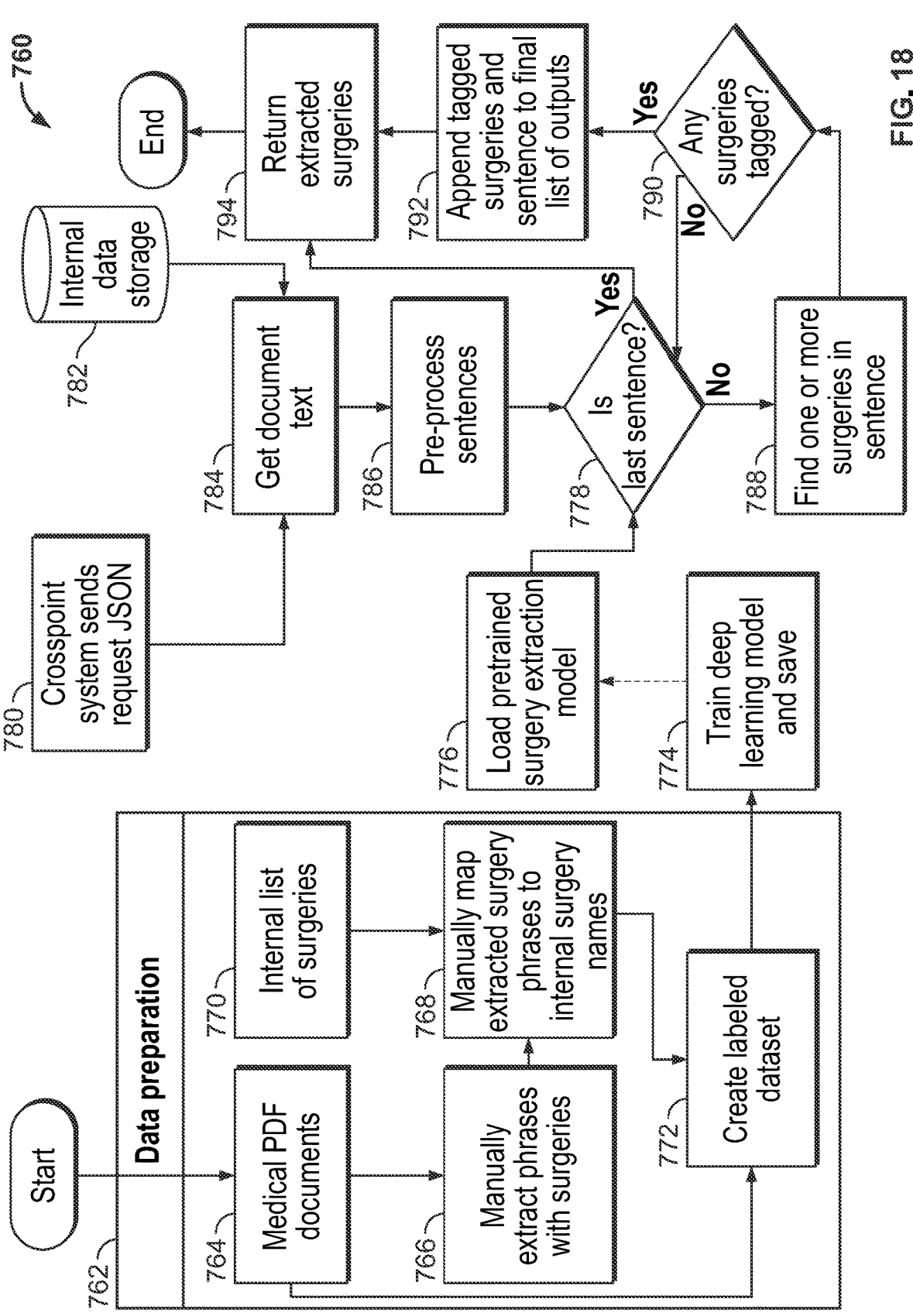
FIG. 18 is flowchart illustrating another embodiment of the systems and methods of the present disclosure, for extracting surgical information from medical records.

FIG. 18 is flowchart illustrating another embodiment of the systems and methods of the present disclosure, indicated generally at 760, for extracting surgical information from medical records. In the medical history of an injured party, past and potential future surgeries may have an impact on the settlement of the claim. It is important for an adjuster to know if any major surgery was performed in the past or recommended for the future and, if such information to be considered when settling the claim. Accordingly, the process steps disclosed in FIG. 18 extract surgical information, including past surgeries and future recommendations, from medical records to assist an adjuster in expediting claim settlements. Initially, in step 762, data preparation steps are performed. Specifically, in step 764, one or more medical documents (e.g., in PDF format) are obtained. Next, in step 766, phrases are extracted from the document that are associated with surgeries. Then, in step 768, extracted surgery phrases are mapped to internal surgery names, using an internal list of surgeries provided in step 770. In step 772, the system creates a labeled dataset that can be used for training.

In step 774, the system trains a deep learning surgery extraction model using the labeled dataset, and saves the trained deep learning model. Then, in step 776, the system loads the trained surgery extraction model. In step 778, a determination is made as to whether the last sentence of a document to be analyzed (e.g., using the trained surgery extraction model) has been reached. In making this determination, the system also factors in processing steps 780-786. Specifically, in step 780, the system sends a JSON request notice, and in step 784, the system obtains document text from internal data storage 782. In step 786, the system pre-processes the sentences. If a negative determination is made in step 778, step 788 occurs, wherein the system finds one or more surgeries in the sentence using the trained surgery extraction model. Then, in step 790, a determination is made as to whether any surgeries have been tagged. If not, control returns to step 778; otherwise, step 792 occurs, wherein the system appends tagged surgeries and the sentence to a final list of outputs. Then, in step 794, the system returns extracted surgeries. If a negative determination is made in step 778, step 794 occurs.

Figure 19:
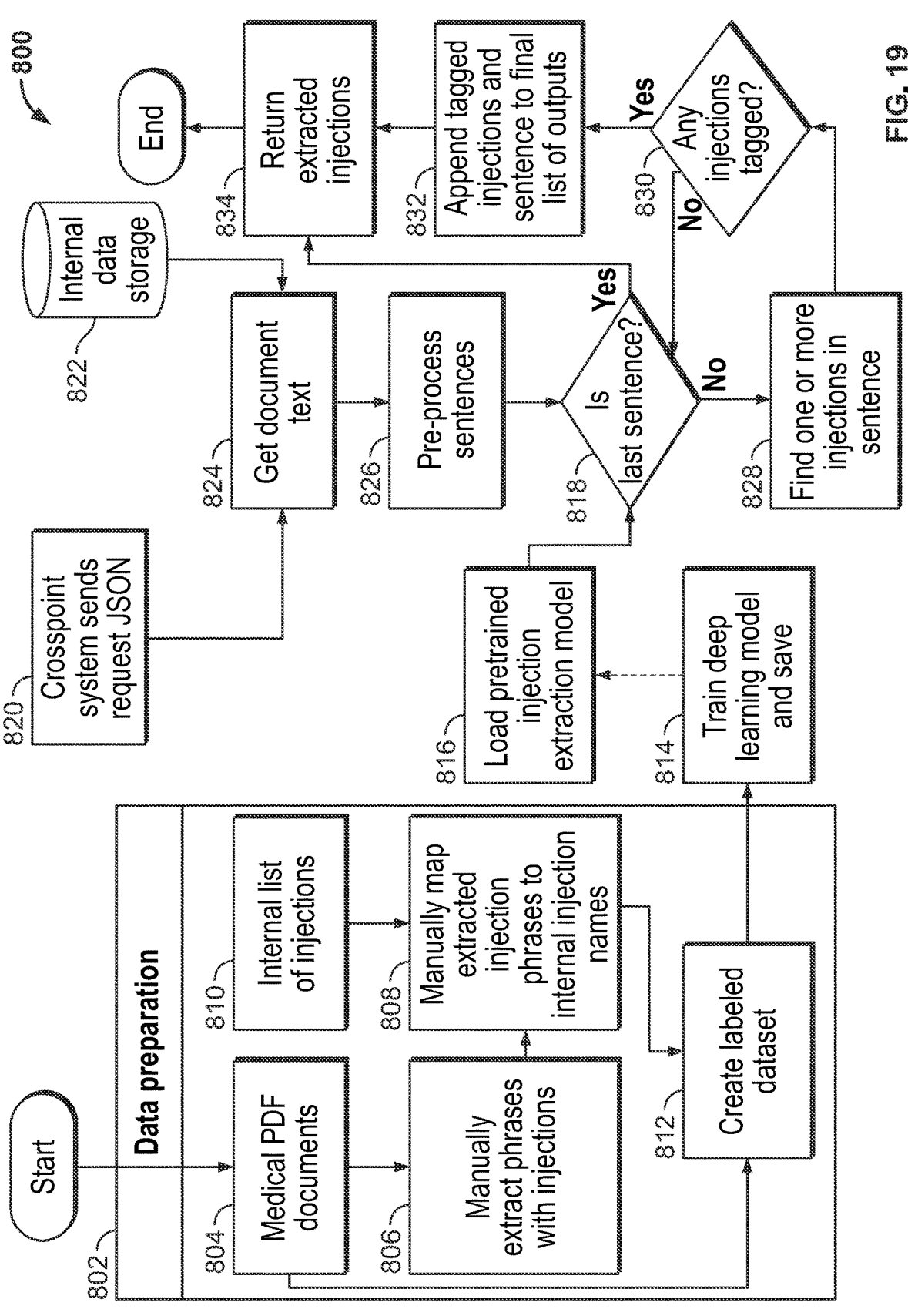
FIG. 19 is a flowchart illustrating another embodiment of the systems and methods of the present disclosure, for extracting injections data from medical records.

FIG. 19 is a flowchart illustrating another embodiment of the systems and methods of the present disclosure, indicated generally at 800, for extracting injections data from medical records. In the medical history of an injured party, past and potential future joint injections may have an impact on the settlement of the claim. It is important for an adjuster to know if any major injections were administered in the past or recommended as potential future treatment and if such information must be considered when settling the claim. Accordingly, the processes of FIG. 19 extract injections data, including previously administered injections and potential future injections, from medical documents to assist an adjuster in expediting claims settlements. Initially, in step 802, data preparation steps are performed. Specifically, in step 804, one or more medical documents (e.g., in PDF format) are obtained. Next, in step 806, phrases are extracted from the document that are associated with injections. Then, in step 808, extracted injection phrases are mapped to internal injection names, using an internal list of injections provided in step 810. In step 812, the system creates a labeled dataset that can be used for training.

In step 814, the system trains a deep learning injection extraction model using the labeled dataset, and saves the trained deep learning model. Then, in step 816, the system loads the trained injection extraction model. In step 818, a determination is made as to whether the last sentence of a document to be analyzed (e.g., using the trained injection extraction model) has been reached. In making this determination, the system also factors in processing steps 820-826. Specifically, in step 820, the system sends a JSON request notice, and in step 824, the system obtains document text from internal data storage 822. In step 826, the system pre-processes the sentences. If a negative determination is made in step 818, step 828 occurs, wherein the system finds one or more injections in the sentence using the trained injection extraction model. Then, in step 830, a determination is made as to whether any injections have been tagged. If not, control returns to step 818; otherwise, step 832 occurs, wherein the system appends tagged injections and the sentence to a final list of outputs. Then, in step 834, the system returns extracted surgeries. If a negative determination is made in step 818, step 834 occurs.

Figure 20:
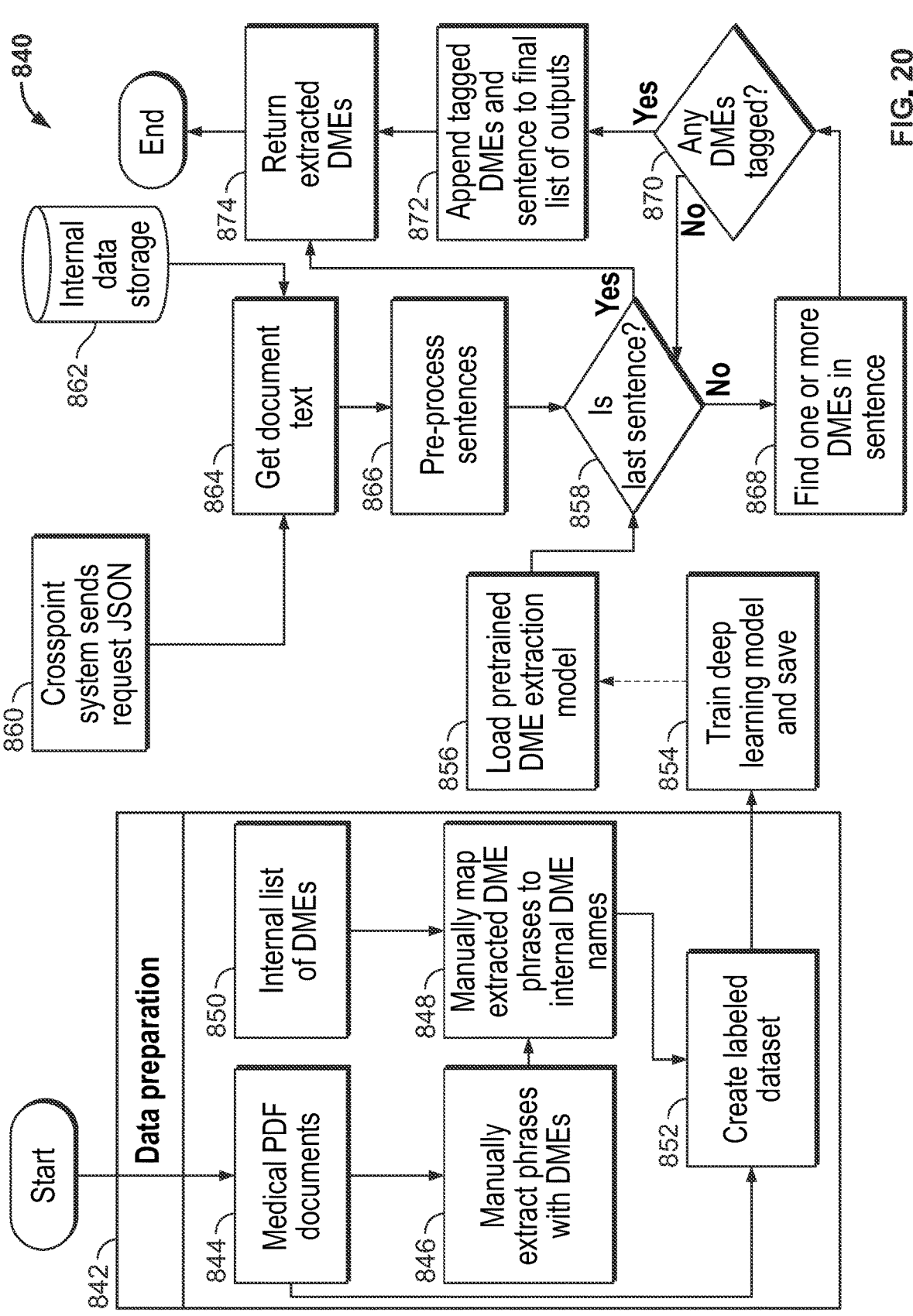
FIG. 20 is a flowchart illustrating another embodiment of the systems and methods of the present disclosure, for extracting DME items from medical records.

FIG. 20 is a flowchart illustrating another embodiment of the systems and methods of the present disclosure, indicated generally at 840, for extracting durable medical equipment (DME) information from medical records. In the medical history of an injured party, past and potential future use of DME may have an impact on the settlement of a claim. It is important for an adjuster to know if DME has been prescribed, used, or is anticipated to be needed in the future treatment of the individual. Accordingly, the processes discussed in connection with FIG. 20 extract DME information (e.g., items) from medical documents to assist an adjuster in expediting claims settlements. Initially, in step 842, data preparation steps are performed. Specifically, in step 844, one or more medical documents (e.g., in PDF format) are obtained. Next, in step 846, phrases are extracted from the document that are associated with DME. Then, in step 848, extracted DME phrases are mapped to internal DME names, using an internal list of DME provided in step 850. In step 852, the system creates a labeled dataset that can be used for training.

In step 854, the system trains a deep learning DME extraction model using the labeled dataset, and saves the trained deep learning model. Then, in step 856, the system loads the trained DME extraction model. In step 858, a determination is made as to whether the last sentence of a document to be analyzed (e.g., using the trained DME extraction model) has been reached. In making this determination, the system also factors in processing steps 860-866. Specifically, in step 860, the system sends a JSON request notice, and in step 864, the system obtains document text from internal data storage 862. In step 866, the system pre-processes the sentences. If a negative determination is made in step 858, step 868 occurs, wherein the system finds one or more DME entries in the sentence using the trained injection extraction model. Then, in step 870, a determination is made as to whether any DME entries have been tagged. If not, control returns to step 858; otherwise, step 872 occurs, wherein the system appends tagged DME entries and the sentence to a final list of outputs. Then, in step 874, the system returns extracted DME entries. If a negative determination is made in step 858, step 874 occurs.

It is noted that the systems and methods of the present disclosure also provide for automatic extraction of other types of information from medical records (e.g., from Medicare Set-Aside (MSA) documents), such as names of service providers, dates of service by such providers, and medical provider specializations. Such features are now described in connection with FIGS. 21-26.

FIG. 21 is a diagram illustrating a medical record to which joint sequence labelling is applied by the systems and methods of the present disclosure, indicated generally at 880. As can be seen, the medical record 880 includes various types of information, such as progress notes (e.g., notes about a patient's progress, made by medical professionals), patient name, provider name, account number, patient date of birth, age, sex, current date, treatment or progress notes, and other information.

FIG. 22 is a diagram illustrating processing steps carried out by the systems and methods of the present disclosure, indicated generally at 882, for joint sequence labelling of the medical record illustrated in FIG. 21. The process 882 allow for joint tagging of both provider names and service dates, and utilizes a named entity recognition approach using sequence labelling for each entity. The process 882 learns classifiers for each entity, and applies a multi-task deep learning model and associated classifiers to each word/token into the entity markers. In step 1, the system creates distributed representations for input into a deep learning-based NER. This can include pre-trained word embeddings, character-level embeddings, POS tags, Gazetteer, etc. In step 2, the system performs context encoding using one or more suitable machine learning processes/networks, such as a CNN, RNN, language model, transformer, etc. In step 3, the system performs tag encoding using one or more suitable encoders, such as Softmax, CRF, RNN, point networks, etc. As shown, the words/tokens can be classified into entity markers such as B for begin, I for intermediate, E for end, O for other, or other suitable entity markers.

Figure 23:
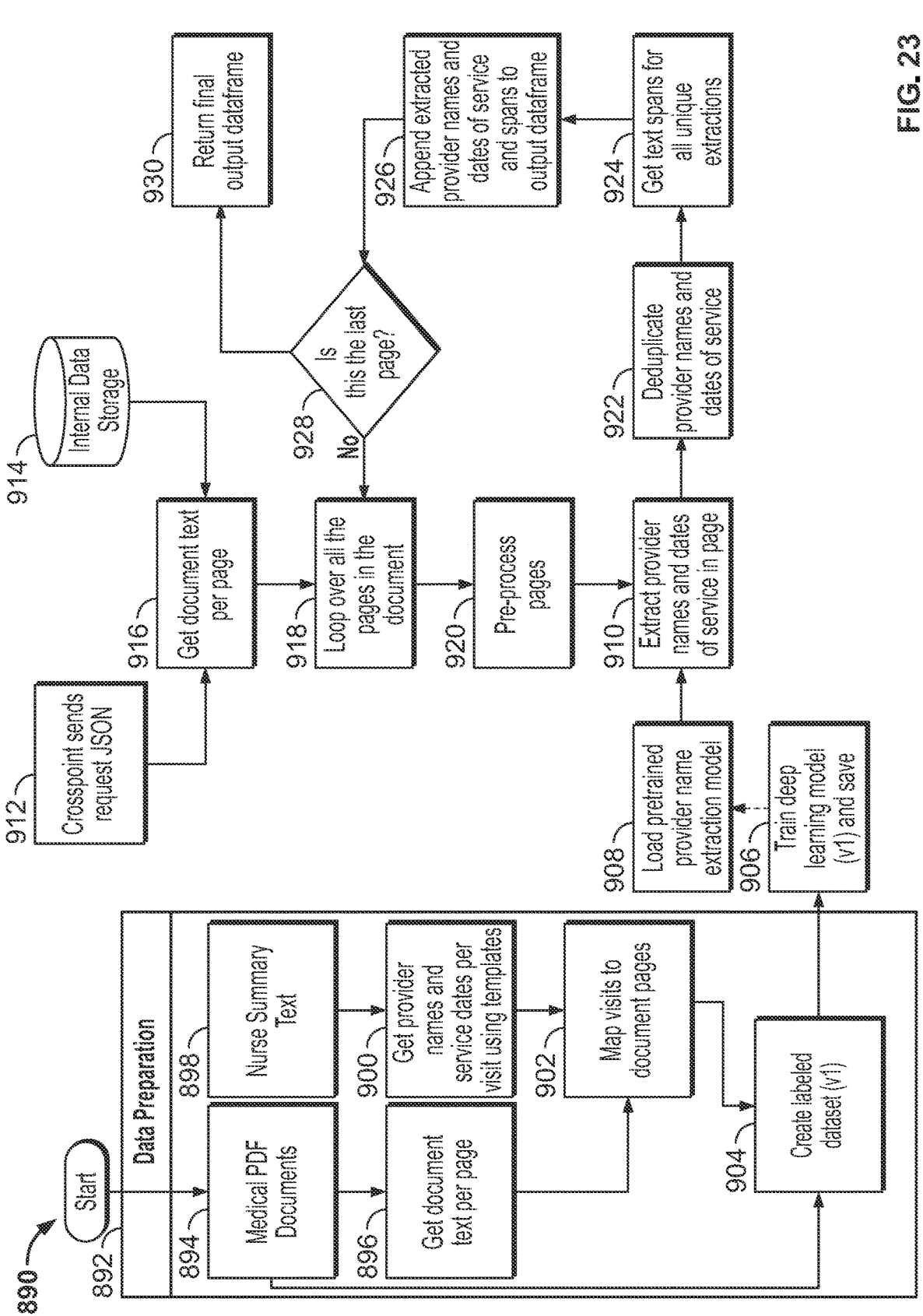
FIG. 23 is a flowchart illustrating additional processing steps carried out by the of the systems and methods of the present disclosure, for joint sequence labeling of provider names and service dates.

FIG. 23 is a flowchart illustrating additional processing steps carried out by the of the systems and methods of the present disclosure, indicated generally at 890, for joint sequence labeling of provider names and service dates. In process 892, data preparation steps are performed. Specifically, in step 894, one or more medical records are obtained, such as one or more PDF documents. Additionally, in step 898, text corresponding to one or more nurse summaries is obtained. In step 896, text from each page of the medical record is retrieved. In step 900, medical provider names and service dates per visit are obtained using one or more pre-defined templates. In step 902, patient visits are mapped to one or more document pages. In step 904, a labeled data set is created.

In step 906, the system trains and saves a medical provider extraction deep learning model using the data set. Then, in step 908, the trained medical provider extraction deep learning model is loaded. In step 910, using the model, provider names and dates of service are extracted from one or more documents of interest. This step is performed using outputs of steps 912-920. Specifically, in step 912, the system sends a JSON request, and in step 916, the system obtains document text (e.g., per page) from a data store 914. In step 918, the system loops over all of the pages in the document. In step 920, the system pre-processes the pages. In step 922, the system de-duplicates provider names and dates of service. Then, in step 924, the system obtains text spans for all unique extractions. In step 926, the system appends the extracted provider names and dates of service and spans to generate an output data frame. In step 928, a determination is made as to whether the last page of the document/text is reached. If not, control returns to step 918; otherwise, step 930 occurs, wherein the system returns the final output data frame.

Figure 24:
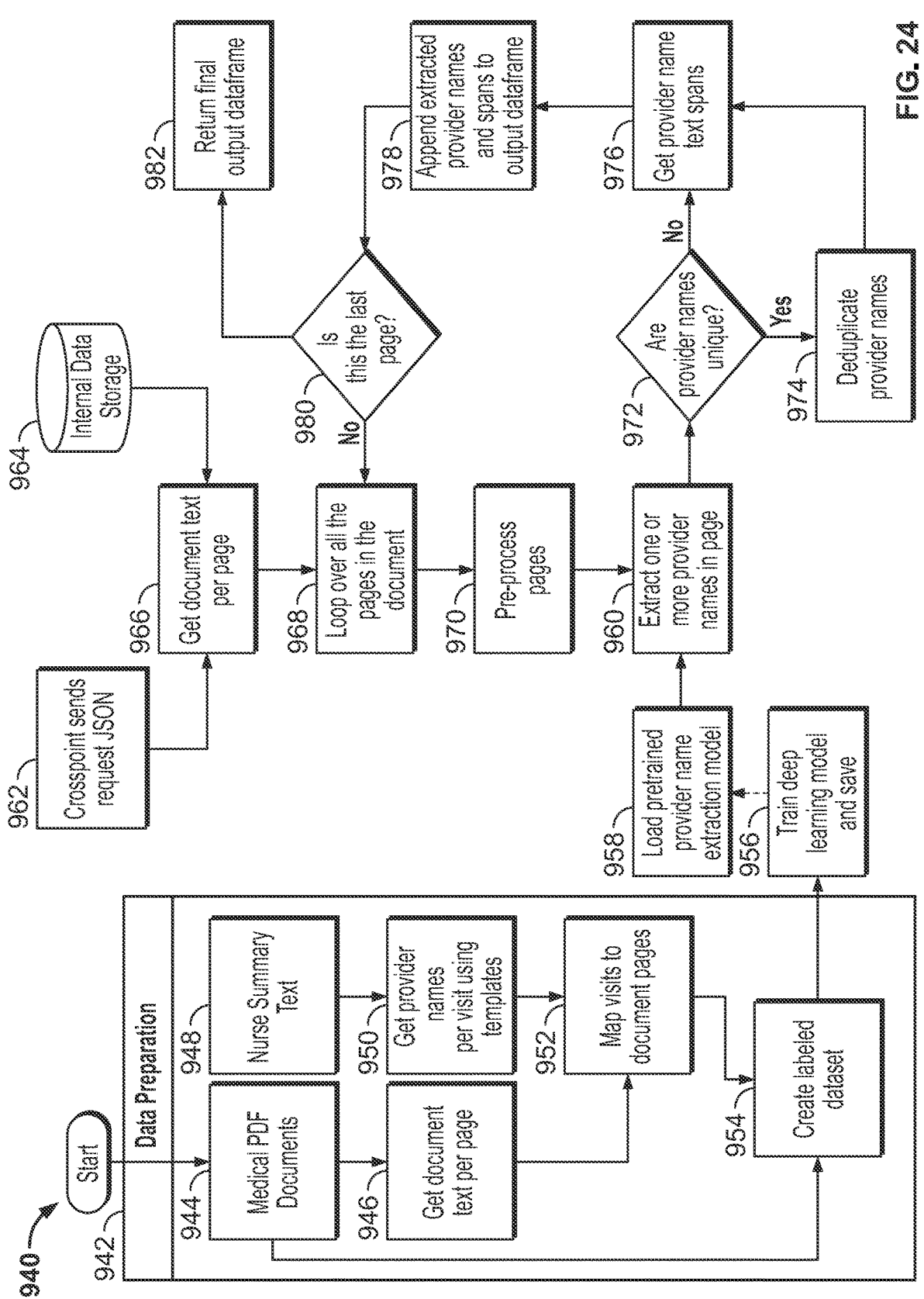
FIG. 24 is a flowchart illustrating additional processing steps carried out by the systems and methods of the present disclosure, for decoupled sequence labelling of provider names.

FIG. 24 is a flowchart illustrating additional processing steps carried out by the systems and methods of the present disclosure, indicated generally at 940, for decoupled sequence labelling of provider names. In process 942, data preparation steps are performed. Specifically, in step 944, one or more medical records are obtained, such as one or more PDF documents. Additionally, in step 948, text corresponding to one or more nurse summaries is obtained. In step 946, text from each page of the medical record is retrieved. In step 950, medical provider names per visit are obtained using one or more pre-defined templates. In step 952, patient visits are mapped to one or more document pages. In step 954, a labeled data set is created.

In step 956, the system trains and saves a medical provider extraction deep learning model using the data set. Then, in step 958, the trained medical provider extraction deep learning model is loaded. In step 960, using the model, provider names are extracted from one or more documents of interest. This step is performed using outputs of steps 962-970. Specifically, in step 962, the system sends a JSON request, and in step 966, the system obtains document text (e.g., per page) from a data store 964. In step 968, the system loops over all of the pages in the document. In step 970, the system pre-processes the pages. In step 972, determines whether the provider names are unique. If not, step 974 occurs, wherein the system de-duplicates the provider names. Otherwise, in step 976, the system obtains text spans for all provider names. In step 978, the system appends the extracted provider names and spans to generate an output data frame. In step 980, a determination is made as to whether the last page of the document/text is reached. If not, control returns to step 968; otherwise, step 982 occurs, wherein the system returns the final output data frame.

Figure 25:
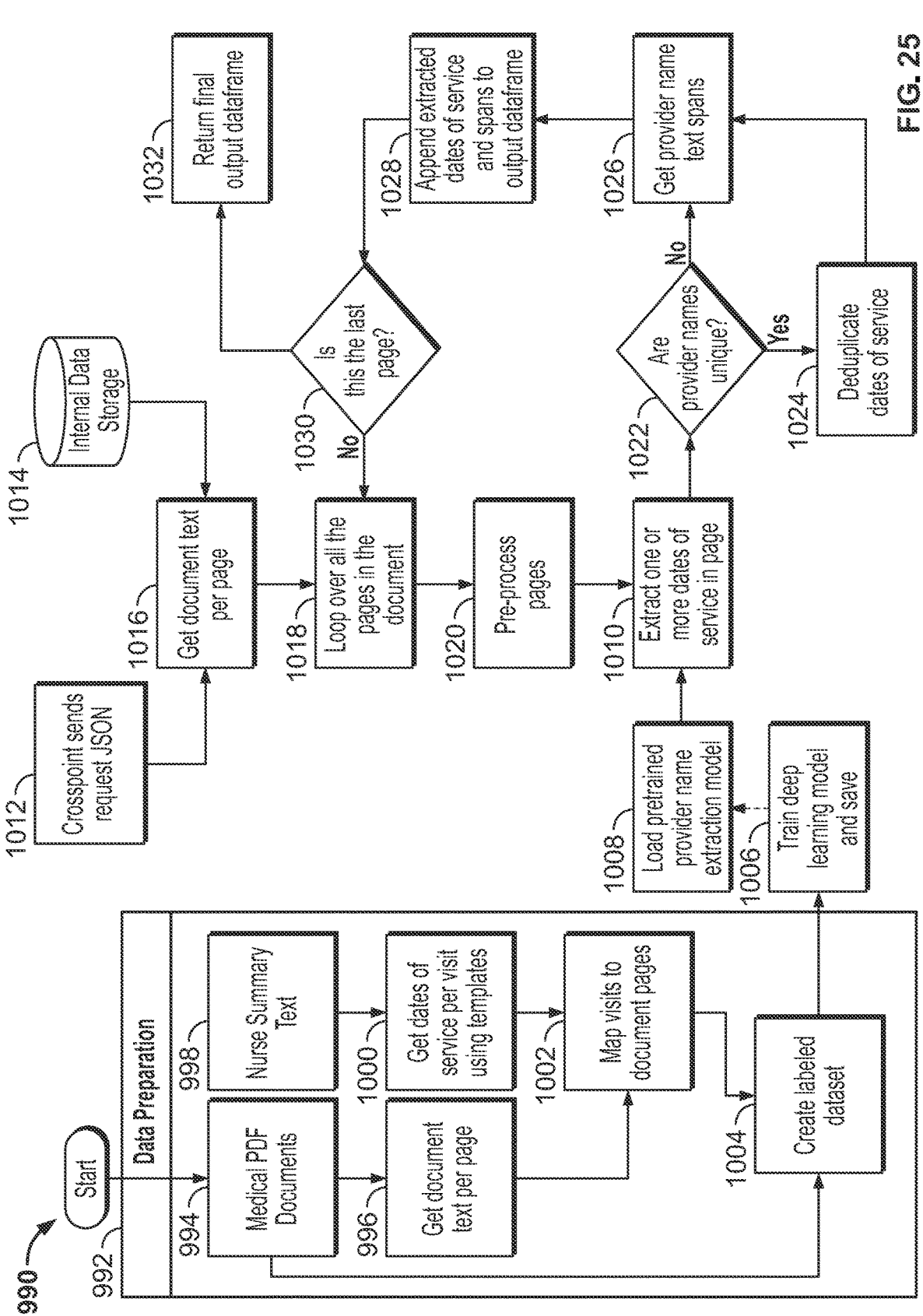
FIG. 25 is a flowchart illustrating additional processing steps carried out by the systems and methods of the present disclosure, for decoupled sequence labelling of dates of service.

FIG. 25 is a flowchart illustrating additional processing steps carried out by the systems and methods of the present disclosure, indicated generally at 990, for decoupled sequence labelling of dates of service. It has been found that provider names and dates of service do not always occur together in MSA documents. As a result, it is beneficial to utilize a decoupled model that increases recall and provides more extractions per target and/or per page, and a more general model that can be deployed in other medical contexts. In process 992, data preparation steps are performed. Specifically, in step 994, one or more medical records are obtained, such as one or more PDF documents. Additionally, in step 998, text corresponding to one or more nurse summaries is obtained. In step 996, text from each page of the medical record is retrieved. In step 1000, dates of service per visit are obtained using one or more pre-defined templates. In step 1002, patient visits are mapped to one or more document pages. In step 1004, a labeled data set is created.

In step 1006, the system trains and saves a medical provider extraction deep learning model using the data set. Then, in step 1008, the trained medical provider extraction deep learning model is loaded. In step 1010, using the model, one or more dates of service are extracted from one or more documents of interest. This step is performed using outputs of steps 1012-1020. Specifically, in step 1012, the system sends a JSON request, and in step 1016, the system obtains document text (e.g., per page) from a data store 1014. In step 1018, the system loops over all of the pages in the document. In step 1020, the system pre-processes the pages. In step 1022, determines whether the provider names are unique. If not, step 1024 occurs, wherein the system de-duplicates the dates of service. Otherwise, in step 1026, the system obtains text spans for all provider names. In step 1028, the system appends the extracted dates of service and spans to generate an output data frame. In step 1030, a determination is made as to whether the last page of the document/text is reached. If not, control returns to step 1018; otherwise, step 1032 occurs, wherein the system returns the final output data frame.

Figure 26:
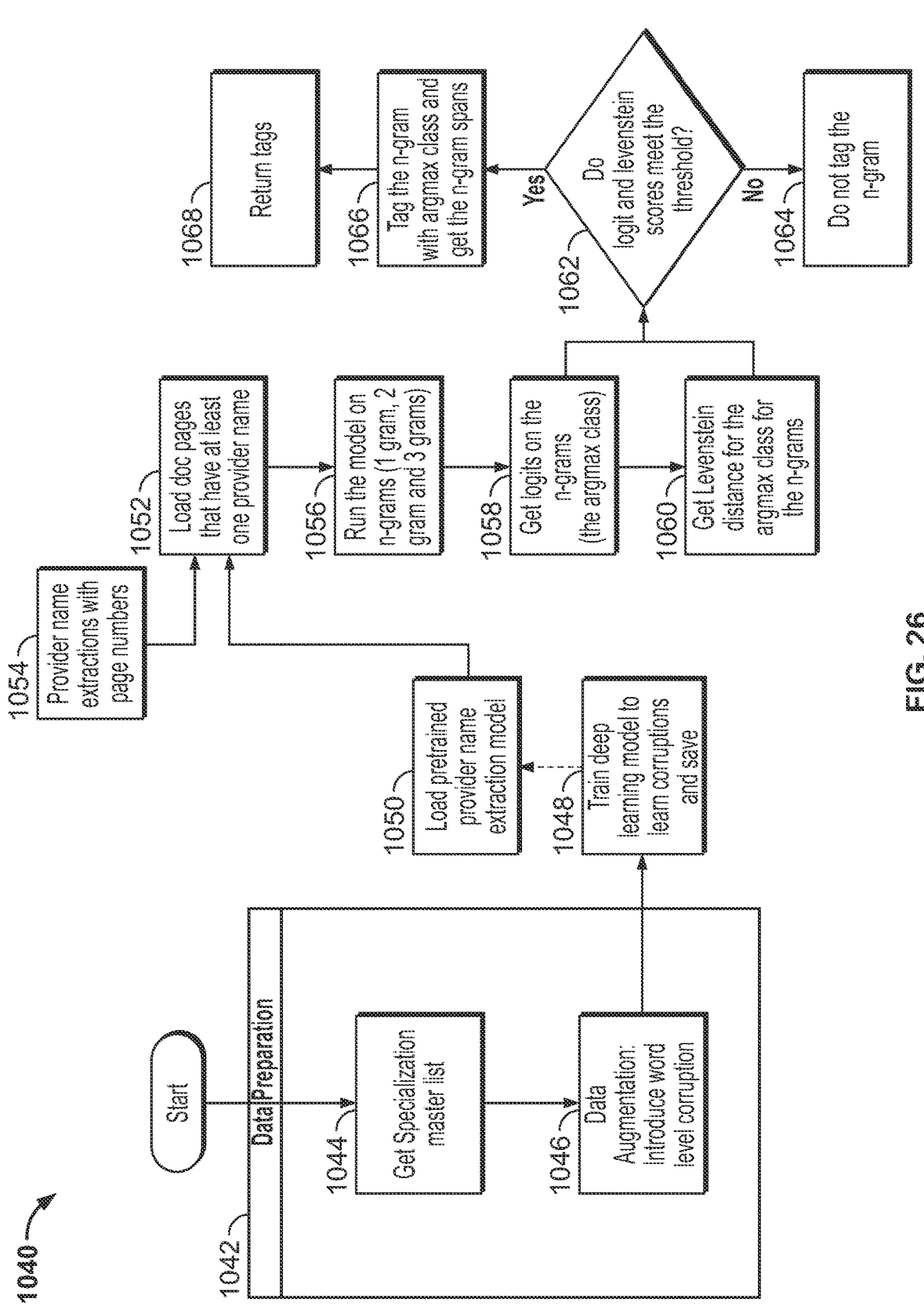
FIG. 26 is a flowchart illustrating additional processing steps carried out by the systems and methods of the present disclosure, for extracting medical provider specialization data from medical records.

FIG. 26 is a flowchart illustrating additional processing steps carried out by the systems and methods of the present disclosure, indicated generally at 1040, for extracting medical provider specialization data from medical records. The process steps 1040 provide a deep learning system that detects variations in provider specializations uniformly, and post-processes results using dictionary-based similarity matching to improve robustness. In process 1042, the system performs data preparation steps. Specifically, in step 1044, the system obtains a specialization master list. Next, in step 1046, data augmentation is performed to introduce word-level corruption. In step 1048, a provider name extraction deep learning model is trained using the augmented data. In step 1050, the system loads the provider name extraction model. In step 1052, the system loads document pages that have at least one provider name. Such information can be obtained in step 1054 from provider name extractions with page numbers. In step 1056, the system runs the extraction model on n-grams (e.g., 1-gram, 2-gram, and 3-grams). In step 1058, the system obtains logits on the n-grams (e.g., using the argmax class). In step 1060, the system obtains the Levenstein distance for the argmax class for the n-grams. In step 1062, a determination is made as to whether the logit and Levenstein scores meet a pre-defined threshold. If a negative determination is made, step 1064 occurs, wherein the system does not tag the n-gram. Otherwise, step 1066 occurs, wherein the system tags the n-gram with argmax class and obtains the n-gram spans. Then, in step 1068, the system returns the tags.

FIG. 27 is a flowchart illustrating additional processing steps, indicated generally at 1080, carried out by the systems and methods of the present disclosure for date extraction and sorting of medical records. Beginning in step 1082, the system retrieves documents having pages of text. Next, data cleaning process 1084 occurs, as well as date of service extraction process 1098, discussed below. The data cleaning process 1084 begins in step 1086, wherein the system removes any e-mail addresses or links that exist in the pages of text. Next, in step 1088, the system removes all non-English words and punctuation marks from the text pages. Then, in step 1090, the system removes any stop words from the pages of text. In step 1092, the system removes any small-length words from the text pages (e.g., words having 2 or fewer letters). Finally, in step 1094, the system removes extra spaces and lower-case "the" letters from the text pages.

Upon completion of data cleaning process 1084, step 1096 occurs, wherein the system cleans the text of each page in the document. Such step could include, but is not limited to, removing or correcting mis-spelled words in the text pages, or making other corrections/adjustments. Control then passes to start and end page classification process 1104, discussed below, which identifies the starting and ending pages of the text pages using a trained classification machine learning model.

As noted above, date of service extraction process 1098 occurs in parallel with data cleaning process 1086. Date of service extraction process 1098 processes the text pages to identify a date of medical service using a suitable pattern matching algorithm, such as a regular expression ("regex") or rational expression algorithm. Specifically, in step 1100, the system searches surrounding words in the text pages using a few key words (which could be pre-programmed into the system). Then, in step 1102, if the system identifies a date in the surrounding words, the date is extracted by the system. The extracted date is then processed in step 1116 to clean the date and to put it into a pre-defined format (e.g., date/month/year format).

In parallel with the date of service extraction process 1098, a second date of service extraction process 1112 occurs, which extracts a date of medical service from the text pages using a pre-trained machine learning model. Specifically, in step 1114, all dates on the text pages are extracted using such model, which could be the model discussed above in connection with FIG. 25. Thereafter, the extracted date is processed in step 1116 discussed above, in order to clean the date and to put it into a pre-defined format.

Start and end page classification process 1104 processes the text pages to identify the starting and ending pages for a particular medical event. Specifically, in step 1106, the system labels the data using three classes, namely, "start page," "end page," and "other." Then, in step 1108, the system tokenizes the input using a customized token. A maximum token length such as 129 (or other value) could be utilized, and the input could be truncated (e.g., using the first 83 tokens and the last 45 tokens). Finally, in step 1110, for each page, the system assigns a label of either "start page," "end page," or "other" to the page.

Post-processing process 1118 is executed by the system after steps 1116 and 1110 discussed above. Specifically, in step 1120, the system uses the start and end labels identified by the start and end page classifier model in process 1104 to bundle the text pages, such that the bundled pages are considered to correspond to the same visit by a patient to a medical provider. Next, in step 1122, for pages in the same bundle, the system counts all of the dates that appear in the same page, using a list of dates generated in step 1116 (and extracted by the processes 1098 and 1112). Then, in step 1124, the system assigns all the pages in the same bundle the same date with a maximum count. Finally, in step 1126, the system generates one date for each page, and processing ends.

Having thus described the system and method in detail, it is to be understood that the foregoing description is not intended to limit the spirit or scope thereof. It will be understood that the embodiments of the present disclosure described herein are merely exemplary and that a person skilled in the art may make any variations and modification without departing from the spirit and scope of the disclosure. All such variations and modifications, including those discussed above, are intended to be included within the scope of the disclosure. What is desired to be protected by Letters Patent is set forth in the following claims.

What is claimed is:

1. A machine learning system for automatically extracting information from medical records, comprising:
a memory storing a plurality of medical records; and
a processor in communication with the memory, the processor programmed to perform the steps of:
retrieving the plurality of medical records from the memory;

retrieving at least one document having pages of text from the plurality of medical records;
processing the pages of text to clean data in the pages of text;
processing the pages of text to extract a date of service from the text using a pattern matching algorithm executed by the processor, the pattern matching algorithm searching for a plurality of surrounding words in the pages of text using at least one key word and identifying and extracting a date from the plurality of surrounding words;
processing the pages of text using a classifier model to identify a type of page for each page of text, the classifier model identifying and labeling each page with a label comprising one of a start page label, and end page label, and an other page label;
bundling the pages of text into a bundle using the labels such that bundled pages are considered to correspond to a visit by a patient to a medical provider;
for each page of each bundle, counting all dates that appear on the same page; and
assigning a date having a maximum count to each page of the bundle.

2. The system of claim 1, wherein the step of processing the pages of text to clean the data in the pages of text comprises removing e-mail addresses and links from the pages of text.

3. The system of claim 2, wherein the step of processing the pages of text to clean the data in the pages of text comprises removing non-English words and punctuation from the pages of text.

4. The system of claim 3, wherein the step of processing the pages of text to clean the data in the pages of text comprises removing stop words from the pages of text.

5. The system of claim 4, wherein the step of processing the pages of text to clean the data in the pages of text comprises removing small-length words from the pages of text.

6. The system of claim 5, wherein the step of processing the pages of text to clean the data in the pages of text comprises removing extra spaces and lower-case "the" letters from the pages of text.

7. The system of claim 1, wherein the step of processing the pages of text to extract the date of service from the text comprises extracting all dates in the page.

8. A machine learning method for automatically extracting information from medical records, comprising:
retrieving a plurality of medical records from a memory;
retrieving at least one document having pages of text from the plurality of medical records;
processing the pages of text to clean data in the pages of text;
processing the pages of text to extract a date of service from the text using a pattern matching algorithm executed by the processor, the pattern matching algorithm searching for a plurality of surrounding words in the pages of text using at least one key word and identifying and extracting a date from the plurality of surrounding words;
processing the pages of text using a classifier model to identify a type of page for each page of text, the classifier model identifying and labeling each page with a label comprising one of a start page label, and end page label, and an other page label;
bundling the pages of text into a bundle using the labels such that bundled pages are considered to correspond to a visit by a patient to a medical provider;

for each page of each bundle, counting all dates that appear on the same page; and assigning a date having a maximum count to each page of the bundle.

9. The method of claim 8, wherein the step of processing the pages of text to clean the data in the pages of text comprises removing e-mail addresses and links from the pages of text.

10. The method of claim 9, wherein the step of processing the pages of text to clean the data in the pages of text comprises removing non-English words and punctuation from the pages of text.

11. The method of claim 10, wherein the step of processing the pages of text to clean the data in the pages of text comprises removing stop words from the pages of text.

12. The method of claim 11, wherein the step of processing the pages of text to clean the data in the pages of text comprises removing small-length words from the pages of text.

13. The method of claim 12, wherein the step of processing the pages of text to clean the data in the pages of text comprises removing extra spaces and lower-case "the" letters from the pages of text.

14. The method of claim 8, wherein the step of processing the pages of text to extract the date of service from the text comprises extracting all dates in the page.

* * * * *